(12) United States Patent
Isailovic et al.

(10) Patent No.: US 10,436,794 B1
(45) Date of Patent: Oct. 8, 2019

(54) PROTOCOL FOR PRECONCENTRATION AND QUANTIFICATION OF MICROCYSTINS USING LC-MS

(71) Applicant: The University of Toledo, Toledo, OH (US)

(72) Inventors: Dragan Isailovic, Toledo, OH (US); Dilrukshika Palagama, Toledo, OH (US); Raymond West, Toledo, OH (US)

(73) Assignee: The University of Toledo, Toledo, OH (US)

( * ) Notice: Subject to any disclaimer, the term of this patent is extended or adjusted under 35 U.S.C. 154(b) by 138 days.

(21) Appl. No.: 15/331,240

(22) Filed: Oct. 21, 2016

(51) Int. Cl.
*G01N 1/40* (2006.01)
*G01N 30/02* (2006.01)
*G01N 33/68* (2006.01)
*G01N 30/72* (2006.01)
*G01N 30/86* (2006.01)

(52) U.S. Cl.
CPC ........ *G01N 33/6848* (2013.01); *G01N 1/405* (2013.01); *G01N 1/4055* (2013.01); *G01N 30/7233* (2013.01); *G01N 30/8679* (2013.01); *G01N 2001/4061* (2013.01); *G01N 2030/027* (2013.01); *G01N 2333/405* (2013.01)

(58) Field of Classification Search
CPC ................................................ G01N 2333/405
See application file for complete search history.

(56) References Cited

PUBLICATIONS

Beck et al. "Fast and Accurate Determination of Algal Toxins in Water Using On-line Preconcentration and UHPLC-HRAM-MS" Oct. 6, 2014, The Column, vol. 10, Issue 18, pp. 2-10 (Year: 2014).*
Spoof et al. "Screening for cyanobacterial hepatotoxins, microcystins and nodularin in environmental water samples by reversed-phase liquid chromatography-electrospray ionisation mass spectrometry" (2003) Journal of Chromatography A, 1020. pp. 105-119 (Year: 2003).*
Eliuk et al., "Evolution of Orbitrap Mass Spectrometry Instrumentation" (2015), Annual Review of Analytical Chemistry, vol. 8, pp. 61-80 (Year: 2015).*

* cited by examiner

*Primary Examiner* — Paul S Hyun
(74) *Attorney, Agent, or Firm* — MacMillan, Sobanski & Todd, LLC

(57) ABSTRACT

Methods for detecting and quantifying one or more microcystin compounds in a sample are described. The methods may include a preconcentration step, and generally utilize an LC-MS or LC-MS/MS analysis with an Orbitrap Fusion mass spectrometer. The methods provide excellent recoveries and limits of quantification of microcystins.

12 Claims, 39 Drawing Sheets

| Time | Module | Event | Parameter |
|---|---|---|---|
| 0.01 | Controller | Start | |
| 2.00 | Pumps | Pump B Conc. | 60 |
| 7.00 | Pumps | Pump B Conc. | 70 |
| 12.00 | Pumps | Pump B Conc. | 90 |
| 14.00 | Pumps | Pump B Conc. | 10 |
| 18.00 | Controller | Stop | |

FIG. 13A – Table 4

| Concentration | | LR | LA | LW | RR | YR | LF |
|---|---|---|---|---|---|---|---|
| Individual | | | | | | | |
| 500 ppq | Recovery | 99.98 | 98.07 | 98.23 | 99.05 | 98.17 | 99.12 |
| | RSD | 2.13 | 3.25 | 1.24 | 3.87 | 2.65 | 1.98 |
| 25 ppt | Recovery | 98.39 | 99.25 | 98.65 | 99.56 | 98.27 | 99.45 |
| | RSD | 2.89 | 1.26 | 2.56 | 3.48 | 2.98 | 2.15 |
| 600 ppt | Recovery | 98.99 | 99.62 | 99.02 | 99.14 | 98.41 | 98.06 |
| | RSD | 2.09 | 3.14 | 2.56 | 2.89 | 2.47 | 4.51 |
| As a Mixture | | | | | | | |
| 500 ppq | Recovery | 98.15 | 98.46 | 98.21 | 98.99 | 98.16 | 99.45 |
| | RSD | 3.45 | 3.56 | 4.15 | 2.99 | 2.98 | 2.48 |
| 200 ppt | Recovery | 98.99 | 99.74 | 99.05 | 98.26 | 98.45 | 98.05 |
| | RSD | 2.78 | 4.69 | 3.87 | 3.85 | 3.41 | 3.96 |
| | Recovery | 98.26 | 98.56 | 98.47 | 98.26 | 99.15 | 98.58 |
| 600 ppt | RSD | 3.89 | 3.48 | 4.63 | 4.12 | 3.79 | 3.02 |

FIG. 16 – Table 5

| MS method | Data acquisition mode | SPE percent recover (%) | Linear range (µg/L) | R² | LOD (µg/L) | LOQ (µg/L) |
|---|---|---|---|---|---|---|
| QqQ-MS/MS | MRM | - | 9.94-994.55 | 0.9952 | 7.96 | 24.36 |
| LIQ Orbitrap-MS/MS | SRM | - | 497.27-945.49 | 0.9763 | 149.18 | 517.16 |
| Orbitrap-full scan | Full scan | 113.7 | 0.1-1.0 | 0.9991 | 0.009 | 0.03 |
| QqQ-MS/MS | MRM | 88.0-98.0 | 0.5-10.0 | 0.999 | 0.11 | 0.029 |
| QqQ-MS/MS | MRM | 95.0-105.0 | 0.1 - 1 | 0.9997 | 0.012 | 0.04 |
| Ion trap-MS/MS[a] | MRM | 73.5-82.7 | 0.82-200 | 0.9992 | 4.9 ng/L | 15.8 ng/L |
| Q-ToF-MS/MS | DDA[b] | 80.1-85.0 | 0.1-50.0 | 0.994 | 0.01 | 0.1 |
| Ion trap-MS/MS | SRM | 72.6-96.5 | 10-100 | - | 0.1 | 0.5 |
| QqQ-MS/MS | SRM | 97-113 | 0.025-2.50 | 0.99 | 0.002 | 0.005 |
| LIQ-MS/MS | Full scan | - | 0.05-50 | 0.9994 | 0.025 | 0.05 |
| QqQ-MS/MS | MRM | - | 0.5-70 | 0.996 | 0.1 | 0.5 |
| QqQ-MS/MS | MRM | - | 0.2-20 | 0.9997 | 0.04 | 0.1 |
| QqQ-MS/MS | MRM | 79.8-104.0 | 1-750 | 0.99 | 0.002 | 0.006 |
| QqQ-MS/MS | MRM | - | 1-1000 | 0.9949 | 1.5 | 4.5 |
| Q-MS | | 89-104 | 200-2000 ng/L | 0.997 | 2 ng/L | - |
| LCQ-Ion trap | Full scan | - | 0.1-10 ng/L | 0.9992 | 2.5 ng/L | - |
| Orbitrap-MS | SIM | - | 0.025-10 | 0.9999 | ~0.010 | 0.025 |
| Orbitrap-MS | SIM | 97.55-99.85 | 0.50-35 ng/L | 0.9987 | ~0.30 ng/L | 0.50 ng/L |
| Orbitrap-MS/MS | SIM | - | 0.20-10 | 0.9999 | ~0.1 | 0.2 |
| Orbitrap-MS/MS | SIM | - | 7-35 ng/L | 0.9974 | ~5 ng/L | 7 ng/L |

[a] Negative ion mode
[b] Data dependent analysis
All units are converted in to µg/L

FIG. 20 – Table 6

PROTOCOL FOR PRECONCENTRATION AND QUANTIFICATION OF MICROCYSTINS USING LC-MS

RELATED APPLICATIONS

None.

Figure 11:
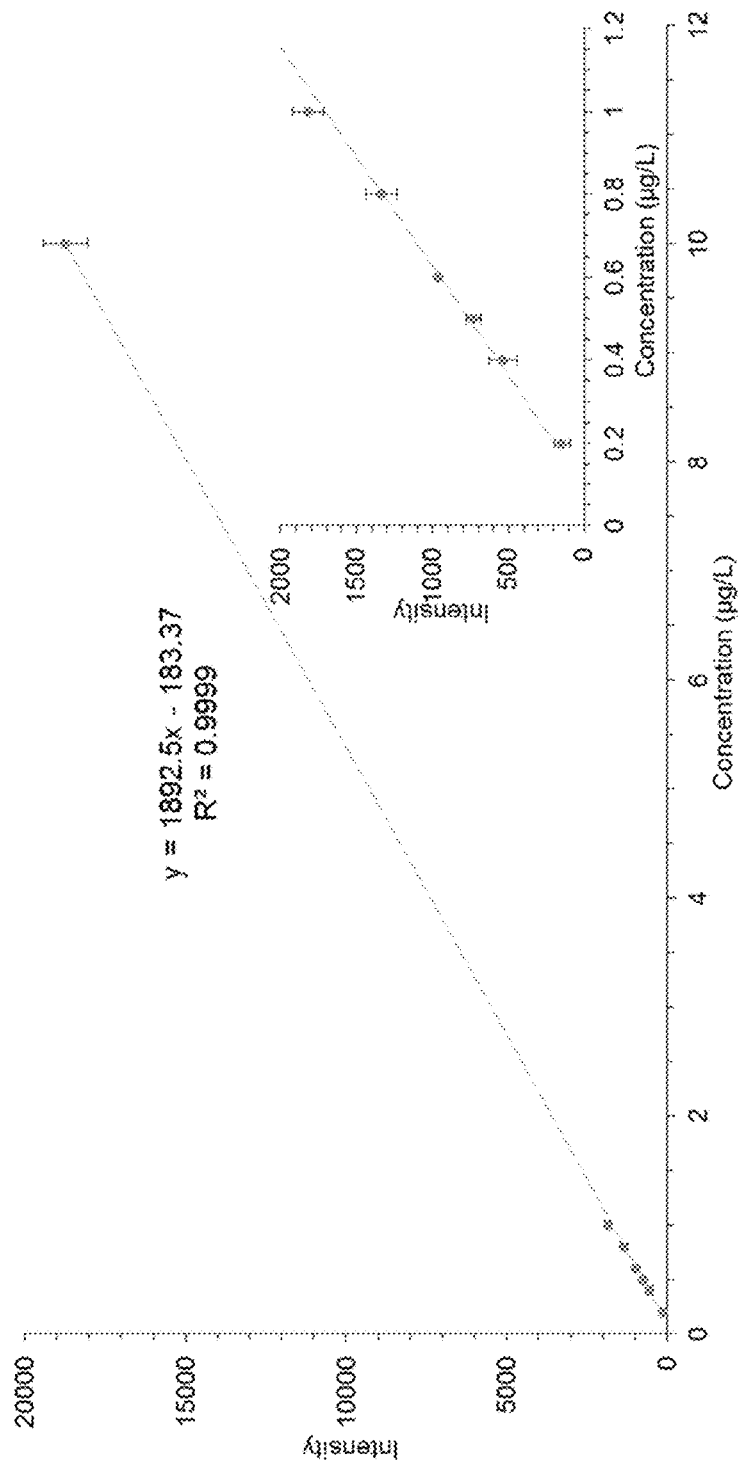

STATEMENT REGARDING FEDERALLY SPONSORED RESEARCH

This invention was made with no government support. The government has no rights in this invention.

BACKGROUND OF THE INVENTION

Cyanobacteria are prokaryotic organisms that typically produce toxic metabolites called cyanotoxins. The most commonly encountered toxic compounds that are released by cyanobacteria are microcystins (MCs). MCs are a group of cyclic heptapeptides which have common amino acid sequences with a recurring motif of a 3-amino-9-methoxy-2,6,8-trimethyl-10-phenyldeca-4,6-dienoic acid (ADDA) group present. At least 150 variants of MCs, such as microcystin-LR (MC-LR), have been identified from different cyanobacterial species. MC-LR is the most common cyanobacterial hepatotoxin, which is often released in water during harmful cyanobacterial blooms.

MCs cause concerns due to both their acute toxicity and chronic effects on humans and wildlife. Due to these concerns, the U.S. Environmental Protecting Agency (EPA) advises that the total concentration of MCs in drinking water should be ≤0.3 μg/L for children, and the state of Minnesota advises an even lower concentration (≤0.1 μg/L) of MC-LR in water. Similarly, the World Health Organization has set a provisional guideline limit for the maximum MC-LR concentration in drinking water of 1 ppb. As a result, robust and sensitive techniques are needed to detected sub-ppb concentrations of MCs in water samples.

MC-LR is one of the most hepatotoxic microcystins released by cyanobacteria. Besides ADDA, the MC-LR structure (FIG. 1) includes a leucine (L) at position 2 and an arginine (R) at position 4 (amino acids in these positions vary from one MC variant to another). In order to monitor the MC-LR concentration in water samples, robust techniques that can detect low concentration of MCs are needed. Determination of MCs is challenging because of a lack of MC standards, inconsistent recoveries during sample preparation, and matrix interferences. Several analytical techniques have been used to detect, identify, and quantify MCs. For example, enzyme-linked immunosorbent assay (ELISA) and protein phosphatase inhibition assay have been used to quantify these toxins. These high-throughput methods typically report total concentration of multiple MC variants, and are therefore limited for the identification and quantification of specific MC variants.

Separations of MCs by HPLC, as well as their detection and quantification, have been demonstrated using UV and fluorescence detectors. LC-MS has been used for the analysis of MCs in water samples since it can provide reliable detection, differentiation, and quantitation of MC congeners. LC-MS and MS/MS detection and quantification of MCs have been reported using several different mass analyzers, such as quadrupole (Q), triple quadrupole (QqQ), ion trap, linear ion trap (LIT), time-of-flight (TOF), and Q-TOF. Most LC-MS/MS quantification methods have been performed using multiple reaction monitoring (MRM) mode of QqQ mass spectrometers.

While LC-MS and LC-MS/MS methods enable highly selective and sensitive quantitation of individual MC variants, they commonly need to utilize some form of preconcentration before the analysis. The preconcentration improves limits of detection (LODs) and limits of quantification (LOQs) of MCs, but it may lead to incomplete or irreproducible recovery of MCs before the LC-MS analysis. Low LOQs (50 ng/L) of MC-LR, MC-YR, and MC-RR have been achieved without preconcentration of the samples before the LC-MS/MS analysis using a LIT MS in full scan mode. Considering the importance of detection and quantification of toxins in drinking water, it is important to continue developing LC-MS and LC-MS/MS methods that can employ modern HPLCs and mass spectrometers for quantification of MCs. There is a need in the art for new and improved methods and systems for the detection and quantification of MCs, such as MC-LR.

SUMMARY OF THE INVENTION

Provided is an improved method of detecting and quantifying a microcystin compound in a sample, the method comprising preconcentrating a sample containing a microcystin compound at a first concentration through a solid phase extraction (SPE) to obtain a preconcentrated sample containing the microcystin at a second concentration, where the second concentration is higher than the first concentration, and conducting a quantitative analysis on the preconcentrated sample to quantify the amount of microcystin in the preconcentrated sample, where the quantitative analysis comprises a liquid chromatography step and a mass spectrometry step using an Orbitrap Fusion mass spectrometer, and using a calibration curve to determine the concentration of the microcystin compound in the sample.

In certain embodiments, the sample contains multiple microcystin compounds, and the liquid chromatography step separates the multiple microcystin compounds. In particular embodiments, the liquid chromatography step comprises gradient high-performance liquid chromatography.

In certain embodiments, the preconcetrating comprises conditioning a solid phase extraction cartridge with methanol containing formic acid (such as 90% methanol containing 0.1% formic acid), equilibrating the sample in formic acid (such as 0.1% formic acid), loading the sample in the conditioned solid phase extraction cartridge, and eluting the loaded sample with acetonitrile and formic acid (such as 90% acetonitrile and 0.1% formic acid). In particular embodiments, the preconcentrating further comprises desalting the loaded sample with formic acid prior to eluting the loaded sample with acetonitrile and formic acid (such as 90% acetonitrile and 0.1% formic acid).

In certain embodiments, the method is capable of quantifying the microcystin compound at a concentration in the sample as low as about 500 ppq. In certain embodiments, the microcystin compound is selected from the group consisting of MC-LR, MC-LA, MC-LF, MC-LW, MC-YR, and MC-RR.

Further provided is a method for detecting and quantifying a microcystin compound in a sample, the method comprising separating a microcystin species in a sample containing a plurality of microcystin species through high-performance liquid chromatograph (HPLC), where the HPLC comprises a gradient mobile phase composition created by acetonitrile and 0.1% formic acid, to produce separated microcystin samples, and conducting mass spectrometry on at least one of the separated microcystin samples to quantify the amount of a microcystin species in the at least one separated microcystin sample, where the mass spectrometry uses an Orbitrap Fusion mass spectrometer, and using a calibration curve to determine the concentration of the at least one microcystin species in the sample. In certain embodiments, the plurality of microcystin species includes two or more of MC-LR, MC-LA, MC-LF, MC-LW, MC-YR, and MC-RR.

In certain embodiments, the method further comprises a preconcentrating step prior to the separating, where the preconcentrating step comprises preconcentrating the sample containing the plurality of microcystin species at a first concentration through a solid phase extraction to obtain a preconcentrated sample containing the plurality of microcystin species at a second concentration, where the second concentration is higher than the first concentration. In particular embodiments, the preconcentrating step comprises conditioning a solid phase extraction cartridge with methanol containing formic acid (such as 90% methanol containing 0.1% formic acid), equilibrating the sample in formic acid (such as 0.1% formic acid), optionally desalting the loaded sample with formic acid (such as 0.1% formic acid), loading the sample in the conditioned solid phase extraction cartridge, and eluting the loaded sample with acetonitrile and formic acid (such as 90% acetonitrile containing 0.1% formic acid).

Further provided is a method of preconcentrating microcystin in a sample, the method comprising conditioning a solid phase extraction cartridge with methanol containing formic acid (such as 90% methanol containing 0.1% formic acid), loading a sample containing a microcystin at a first concentration onto the solid phase extraction cartridge, eluting the sample with acetonitrile containing formic acid (such as 90% acetonitrile containing 0.1% formic acid), and collecting the eluted sample, evaporating solvent from the eluted sample to obtain an evaporated sample, and redissolving the evaporated sample in a solvent (such as 90% methanol containing 0.1% formic acid) to obtain a preconcentrated sample, where the preconcentrated sample contains microcystin at a second concentration, the second concentration being greater than the first concentration. In certain embodiments, the method further comprises equilibrating the SPE cartridge with 0.1% formic acid. In certain embodiments, the method further comprises a washing step. In certain embodiments, the method further comprises subjecting the preconcentrated sample to LC-MS analysis. In certain embodiments, the SPE cartridge is a C18 cartridge. In certain embodiments, the sample comprises a plurality of microcystin species. In particular embodiments, the plurality of microcystin species includes two or more of MC-LR, MC-LA, MC-LF, MC-LW, MC-YR, and MC-RR.

Further provided is a method for separating a plurality of microcystin compounds in a mixture, the method comprising introducing a solvent containing a sample mixture into a column filled with a solid adsorbent material, where the sample mixture comprises a plurality of microcystin compounds, using a first pump to pass a first mobile phase through the column, and using a second pump to pass a second mobile phase through the column, thereby creating a gradient mobile phase in the column to separate the plurality of microcystin compounds in the column, and allowing one or more separated microcystin compounds to elute out of the column. In certain embodiments, the first mobile phase comprises acetonitrile and the second mobile phase comprises 0.1% formic acid. In other embodiments, the first mobile phase comprises 0.1% formic acid with 20 mM ammonium formate, and the second mobile phase comprises methanol with 0.1% formic acid. In certain embodiments, the gradient mobile phase is created over 30 minutes by a solvent profile of 10% methanol with 0.1% formic acid for minutes 0-2, 80% methanol with 0.1% formic acid for minutes 2-16, 90% methanol with 0.1% formic acid for minutes 16-22, and 10% methanol with 0.1% formic acid for minutes 22-30. In certain embodiments, the gradient mobile phase is created over 18 minutes by a solvent profile of 10% acetonitrile for minutes 0-2, 60% acetonitrile for minutes 2-7, 70% acetonitrile for minutes 7-12, 90% acetonitrile for minutes 12-14, and 10% acetonitrile for minutes 14-18.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1: The structure of MC-LR and its most intense fragment ion (m/z~135.0810), which is characteristic for MCs.

FIGS. 2A-2B: Extracted ion chromatogram (EIC) of singly-charged protonated MC-LR ion (m/z 995.5587) (FIG. 2A), and LC-mass spectrum of 1 μg/L standard solution of MC-LR (FIG. 2B).

FIG. 3: The LC-ESI-MS calibration curve for quantification of MC-LR in concentration range 25 ng/L-10 μg/L. The MC-LR samples were not preconcentrated before LC-MS analyses. Standard deviations are shown as error bars. The inset shows the region of the calibration curve in the concentration range from 0.025-1.0 μg/L.

FIGS. 4A-4B: The EIC (FIG. 4A) and mass spectrum (FIG. 4B) corresponding to LOQ of MC-LR (25 ng/L) determined by LC-MS. The MC-LR sample analyzed was not preconcentrated.

FIGS. 5A-5B: The LC-MS calibration curves for quantification of MC-LR in tap water (FIG. 5A) and river water (FIG. 5B) after purification of MC-LR standards using SPE and preconcentration. Standard deviations (n=3) are shown as error bars. The MC-LR concentration ranges analyzed were 500 pg/L-35 ng/L for tap water and 2 ng/L-35 ng/L for river water.

FIGS. 6A-6B: The EIC of singly-charged protonated MC-LR ion (m/z 995.5580) (FIG. 6A), and LC-mass spectrum of 20 ng/L standard solution of MC-LR obtained after 50× sample preconcentration (FIG. 6B). After preconcentration, the concentration of MC-LR in this solution was ~1 μg/L.

FIGS. 7A-7B: The EIC (FIG. 7A) and mass spectrum (FIG. 7B) corresponding to LOQ of MC-LR (500 pg/L) determined by LC-MS after 50× sample preconcentration. After preconcentration, the concentration of MC-LR in this solution was ~25 ng/L.

FIG. 8: Overlaid EICs of singly-charged MC-RR, MC-LR, and MC-LA ions with m/z values of 1038.57, 995.56, and 910.49, respectively. Each MC was analyzed by LC-ESI-MS individually.

FIGS. 9A-9B: Mass spectra of singly-charged MC-LA (FIG. 9A) and MC-RR (FIG. 9B) ions.

FIGS. 10A-10B: EIC of MC-LR fragment ion with m/z 135.0808 (FIG. 10A) and MS/MS spectrum of MC-LR ion with m/z 995.5587 (FIG. 10B). The concentration of MC-LR standard used to acquire these data was 1 μg/L.

FIG. 11: The LC-ESI-MS/MS calibration curve for quantification of MC-LR in the concentration range of 200 ng/L-10 µg/L. The MC-LR samples were not preconcentrated before LC-MS analyses. Standard deviations are shown as error bars. The inset shows the region of the calibration curve in the concentration range of 0.2-10.0 µg/L.

Figure 12:
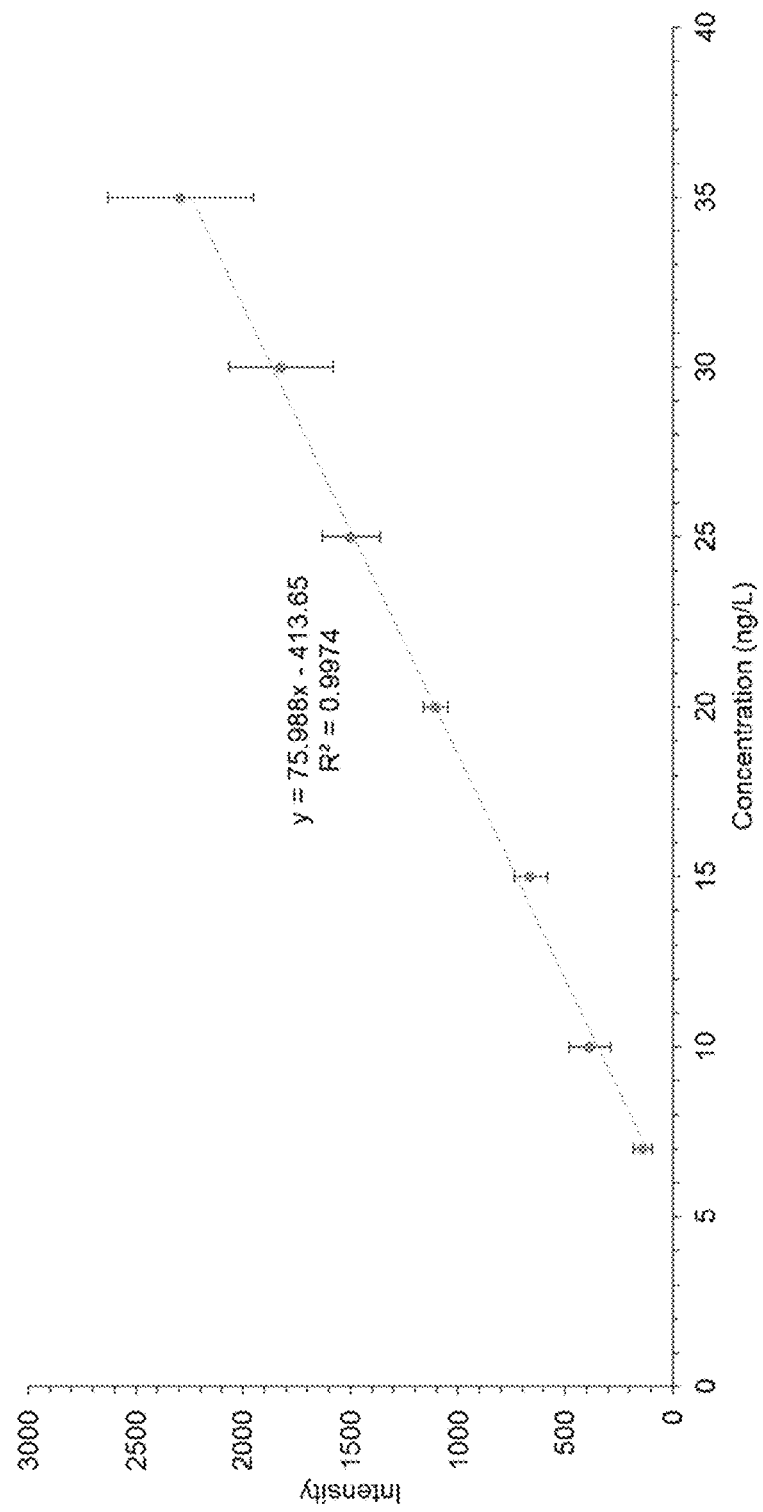

FIG. 12: The LC-MS/MS calibration curve for quantification of MC-LR after 50× preconcentration and purification of MC-LR standards using SPE. Standard deviations are shown as error bars. The MC-LR concentration range analyzed was 7-35 ng/L.

Figure 13B:
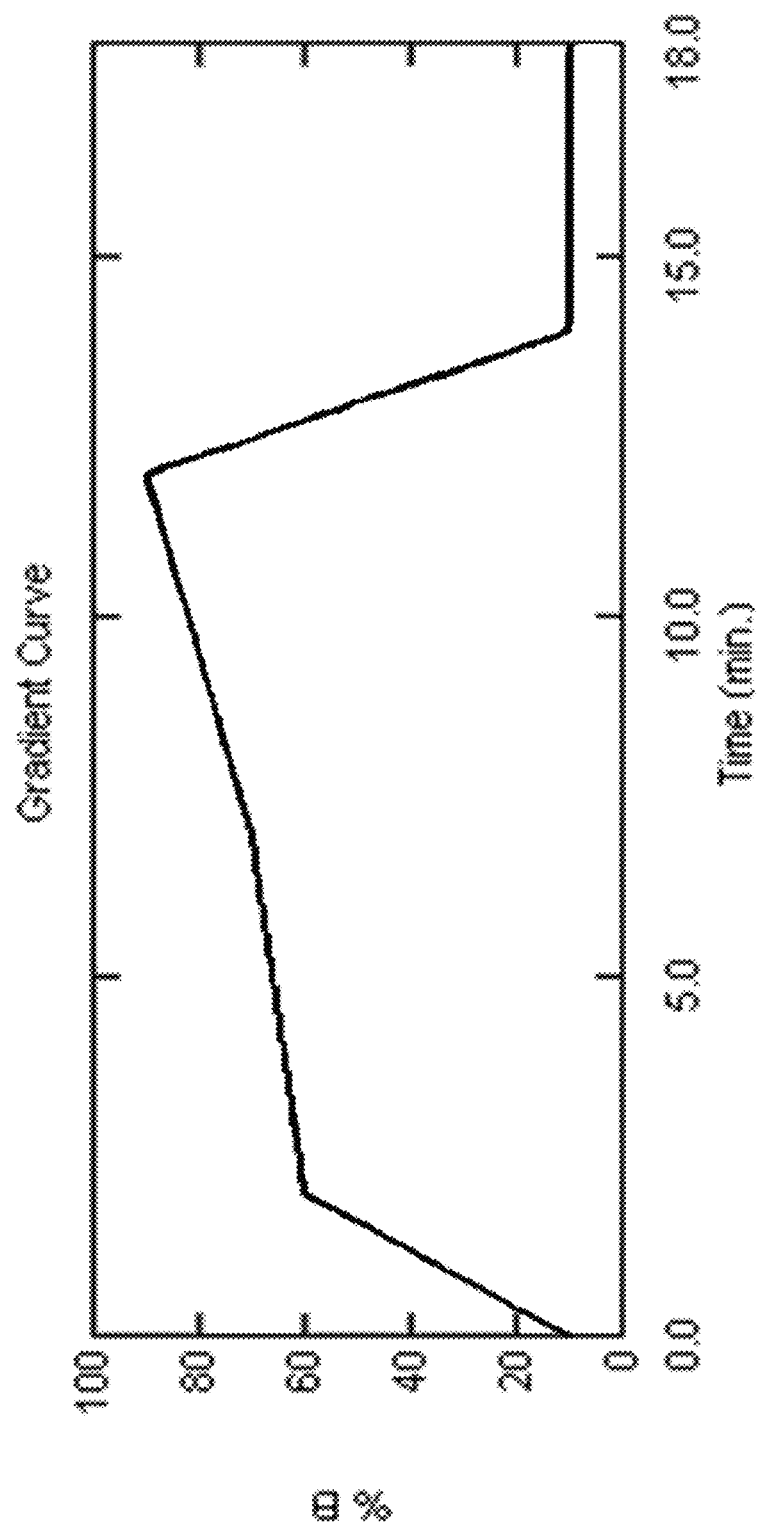

FIGS. 13A-13B: Table 4, showing the solvent parameters for an HPLC method for separation of MCs (FIG. 13A), and a graph showing the solvent gradient in Table 4 (FIG. 13B).

Figure 14:
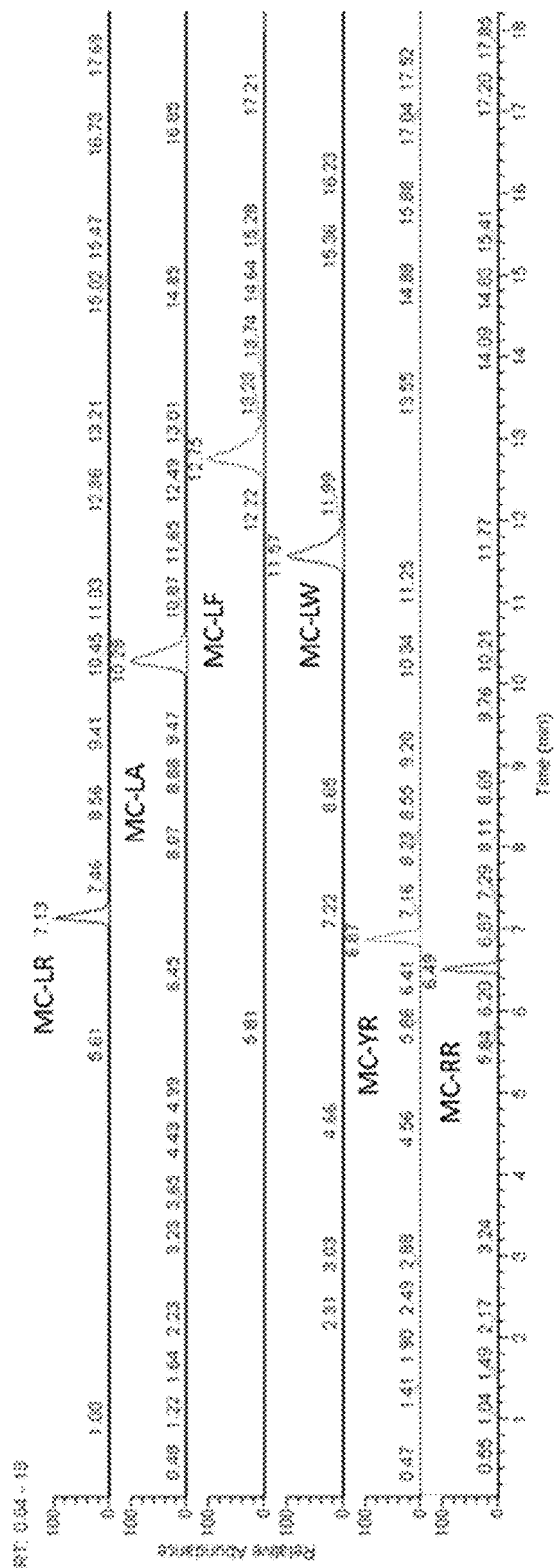
Figure 15A:
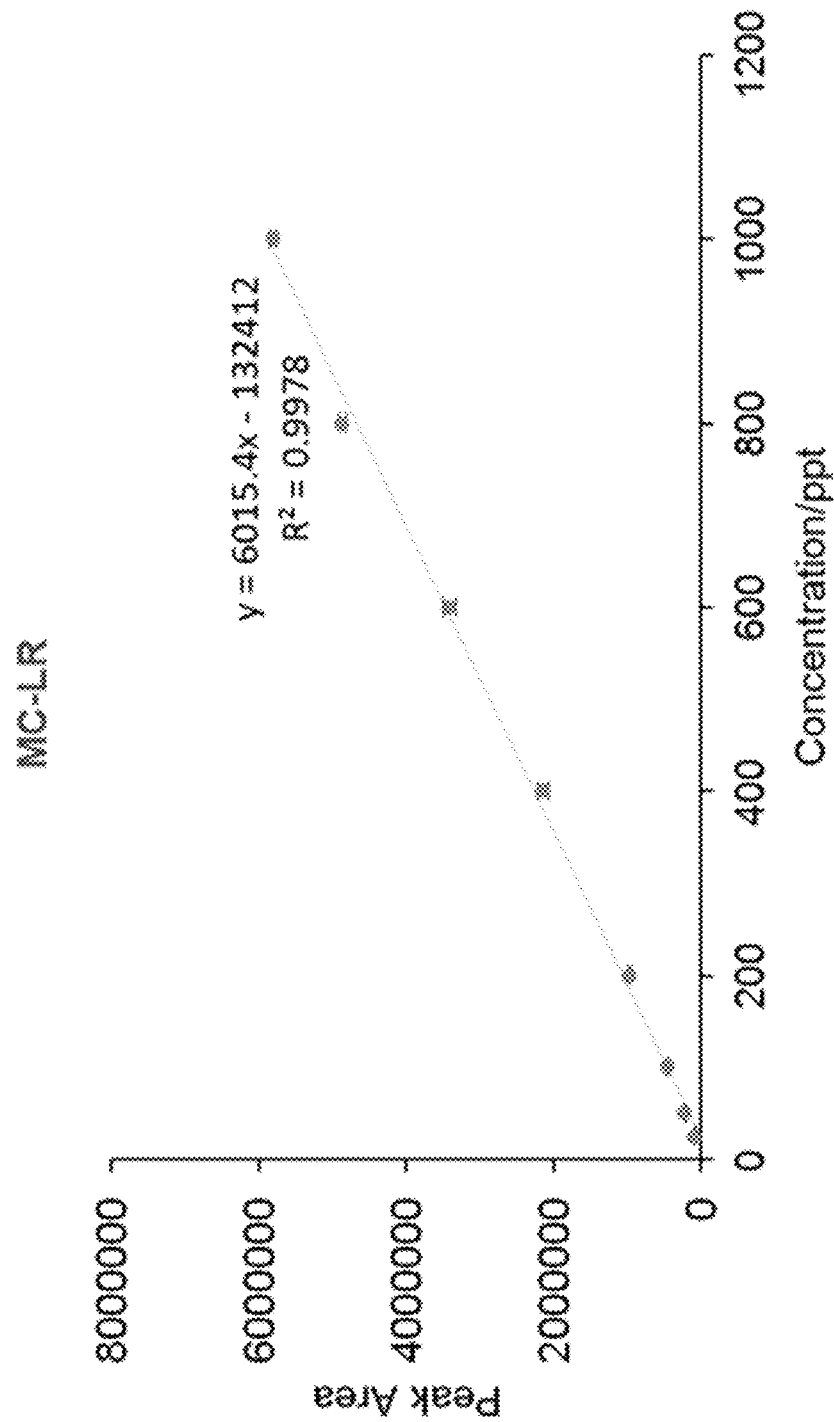
Figure 15B:
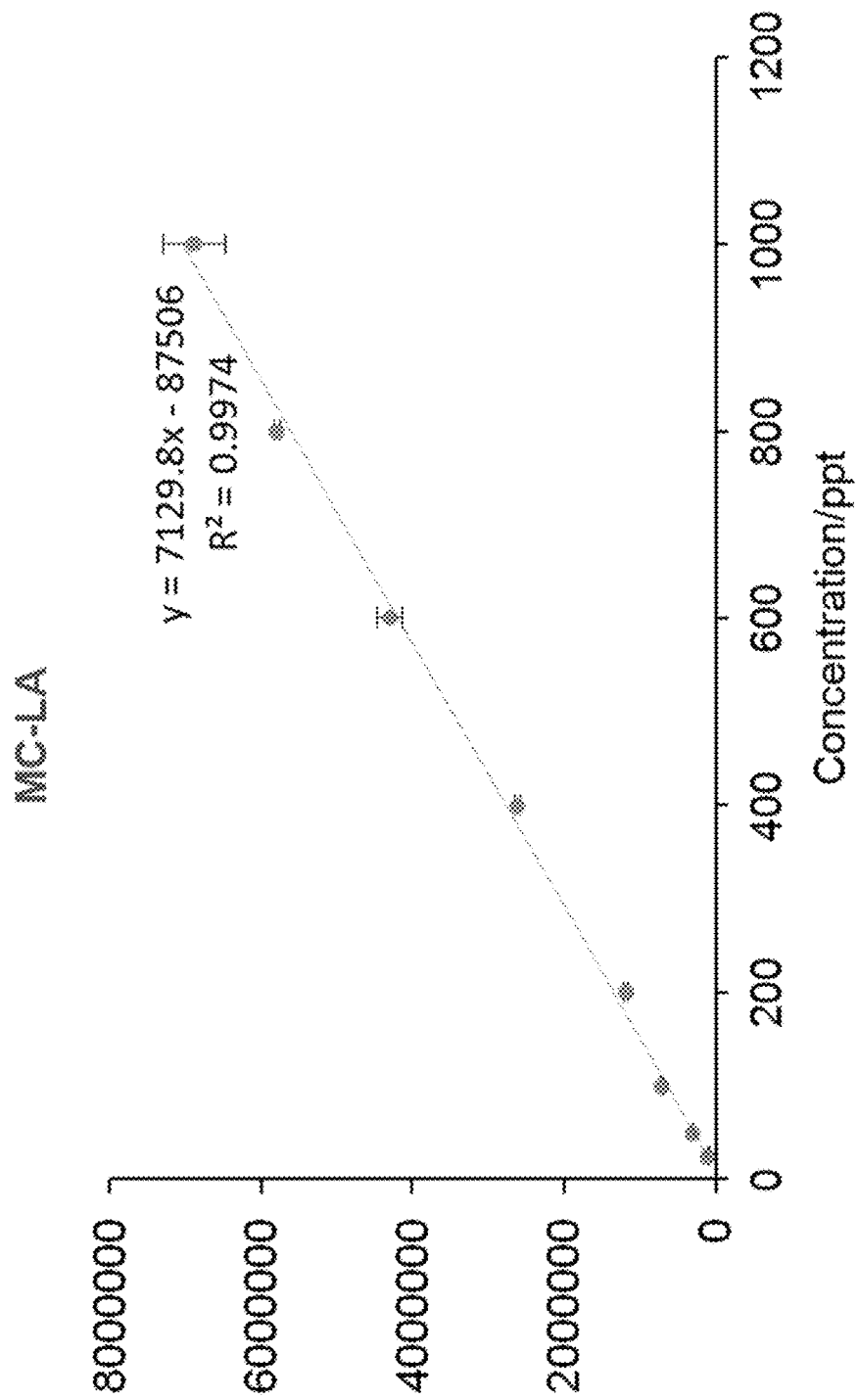
Figure 15C:
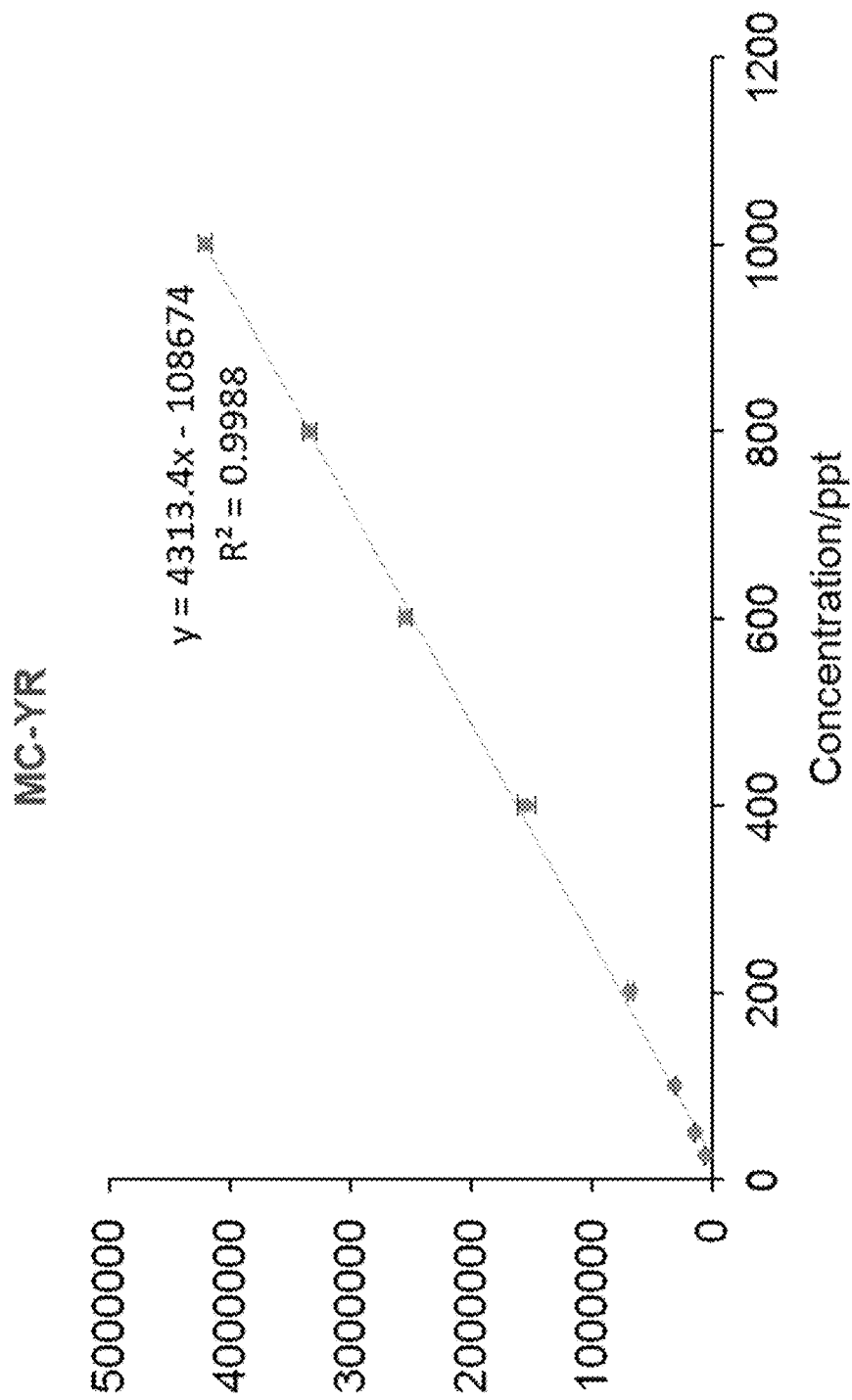
Figure 15D:
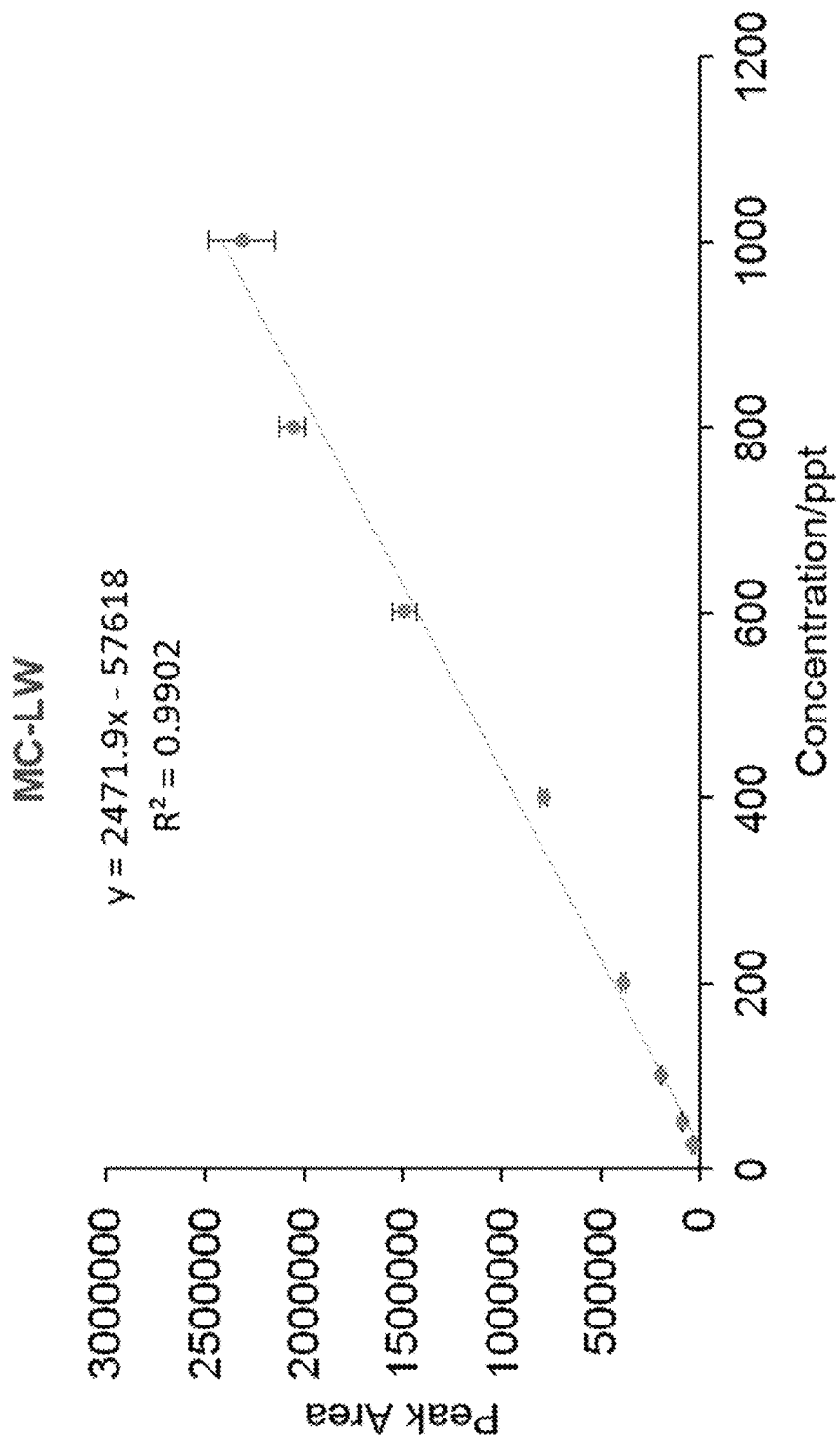
Figure 15E:
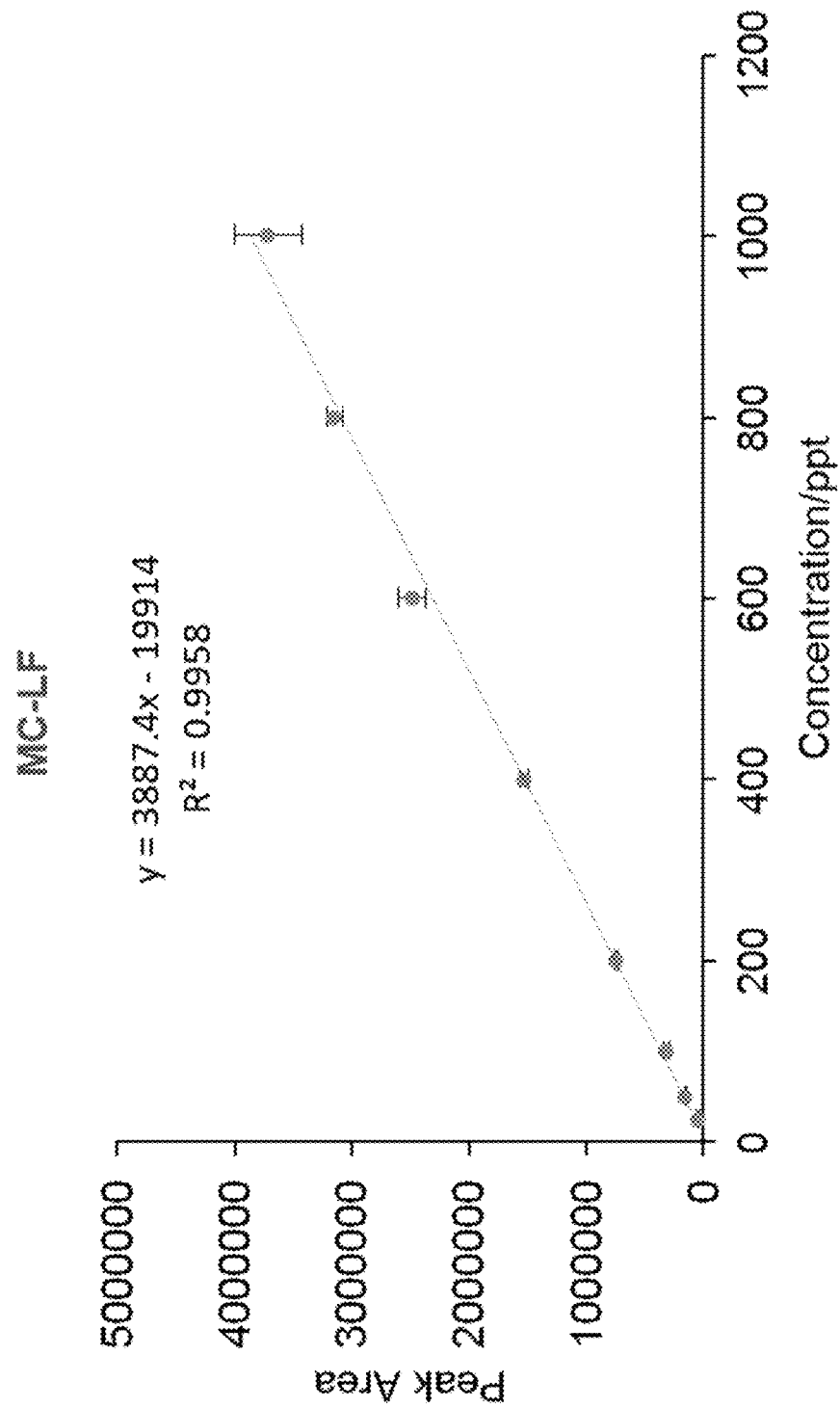
Figure 15F:
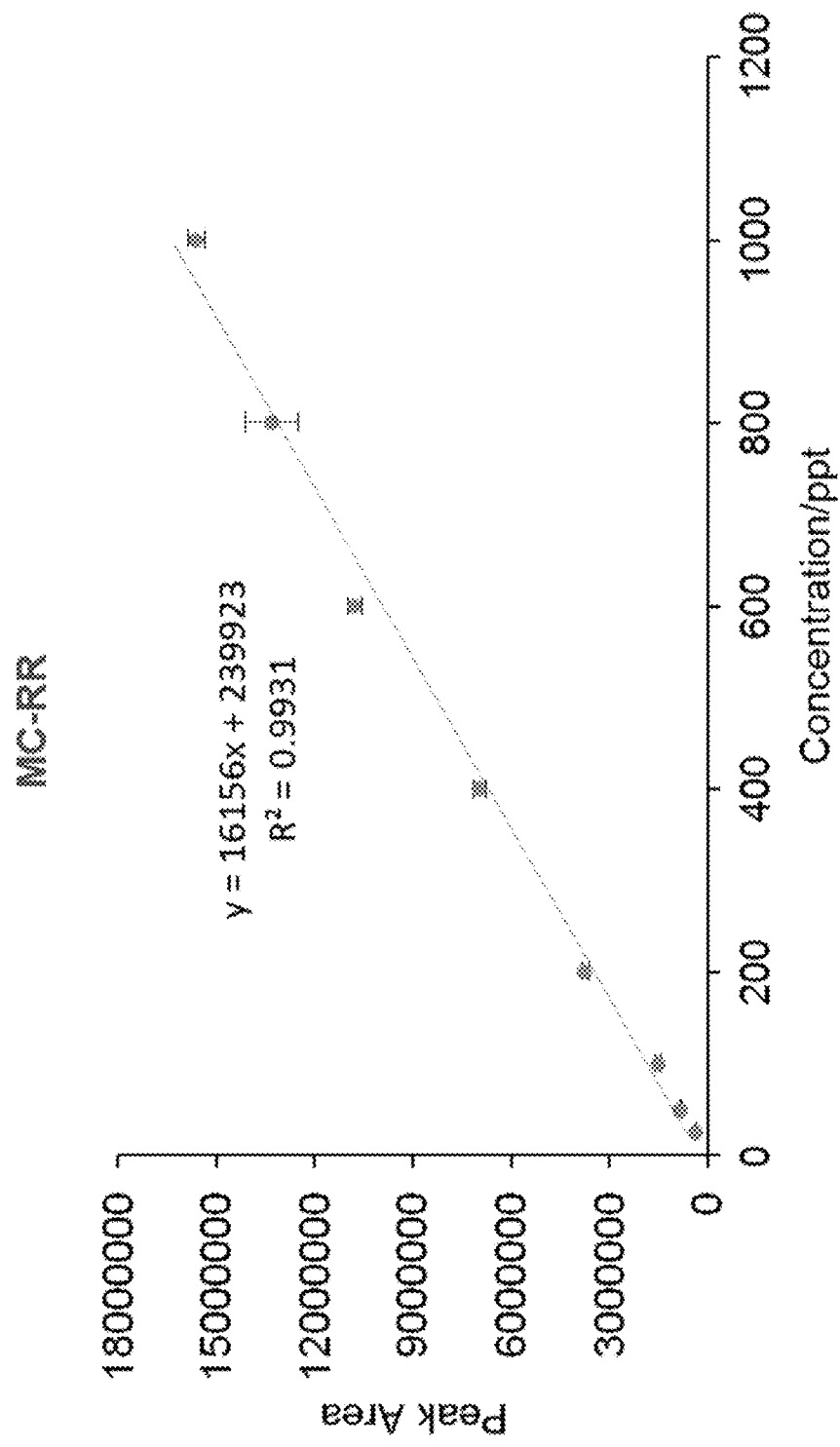
Figure 17A:
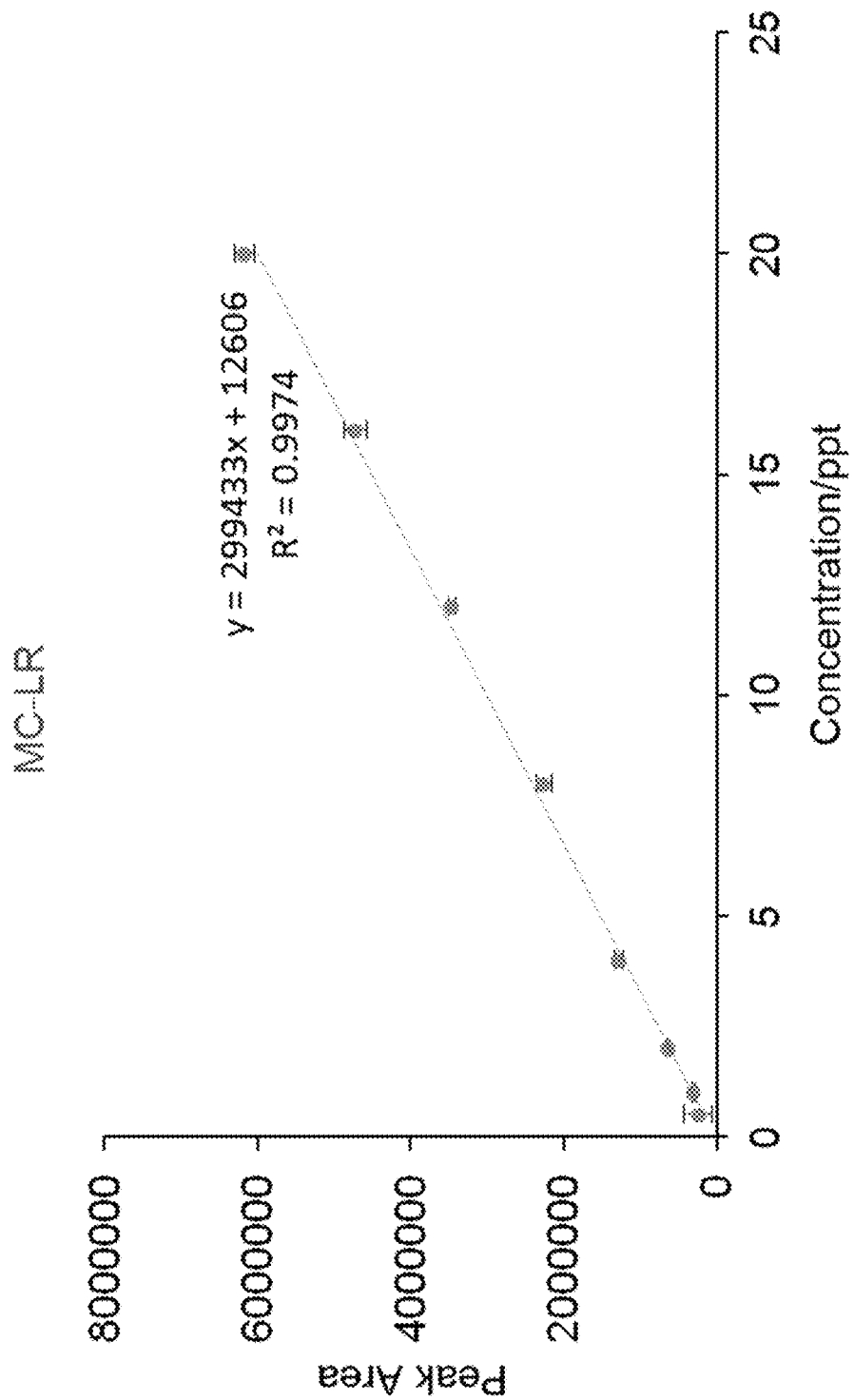
Figure 17B:
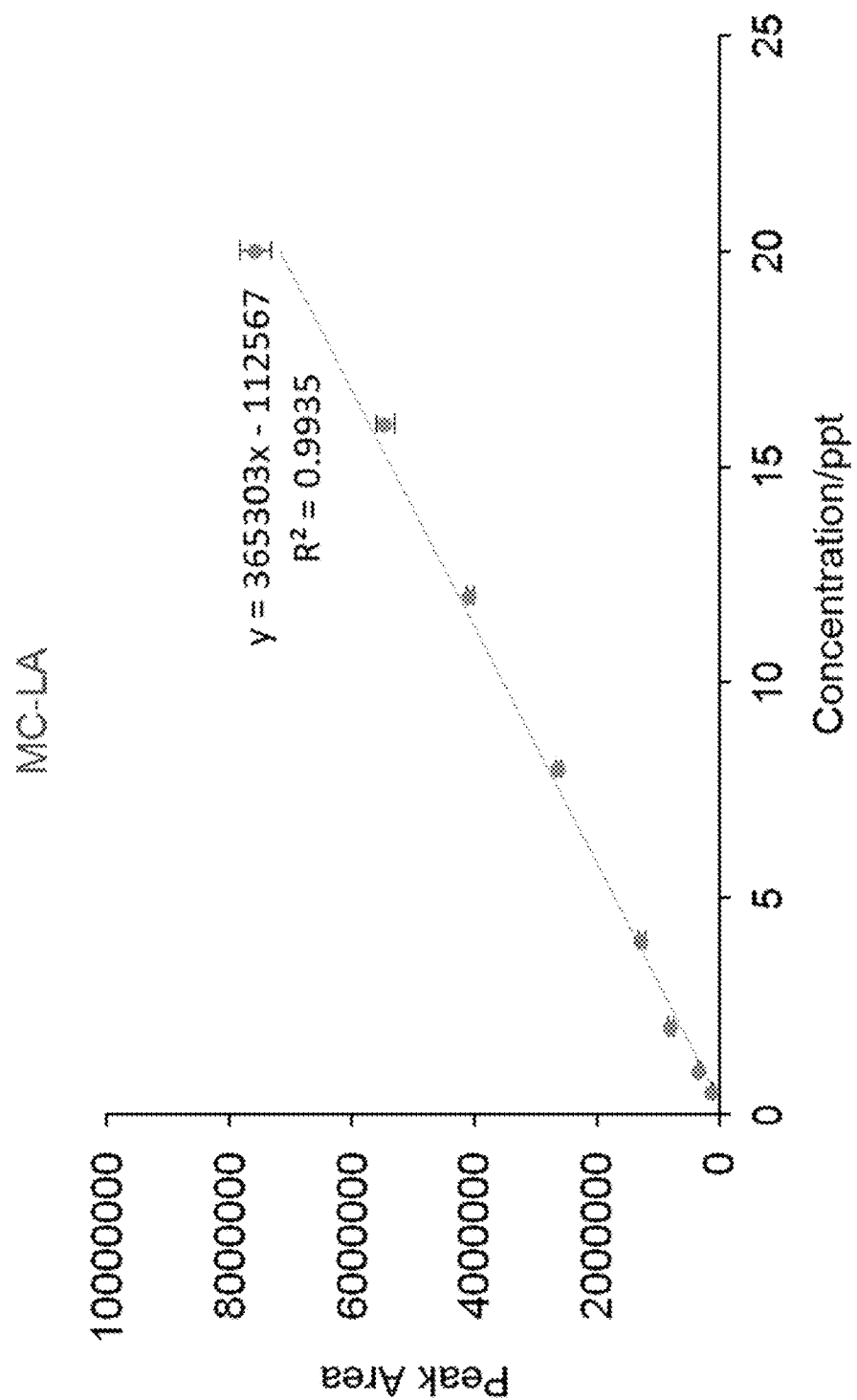
Figure 17C:
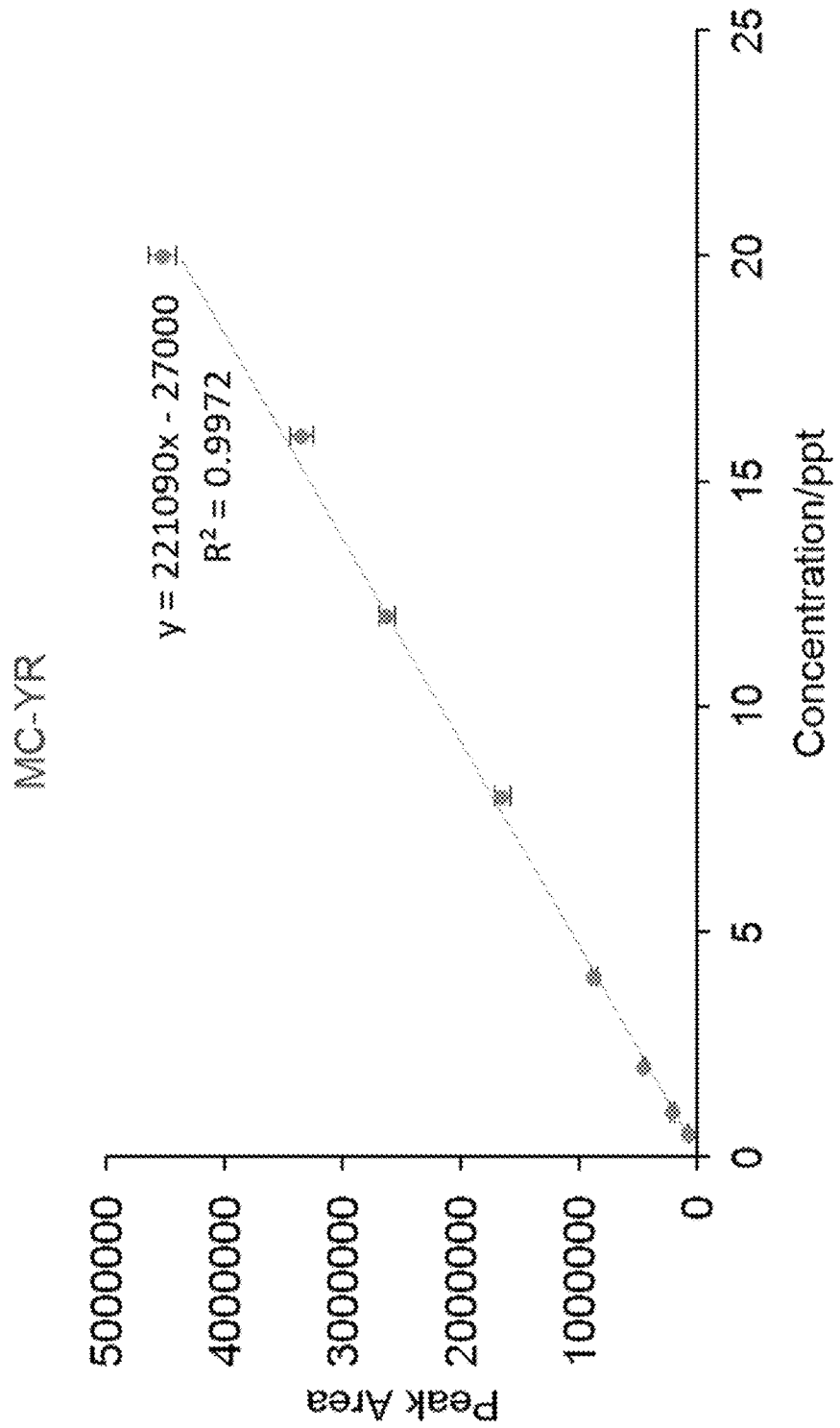
Figure 17D:
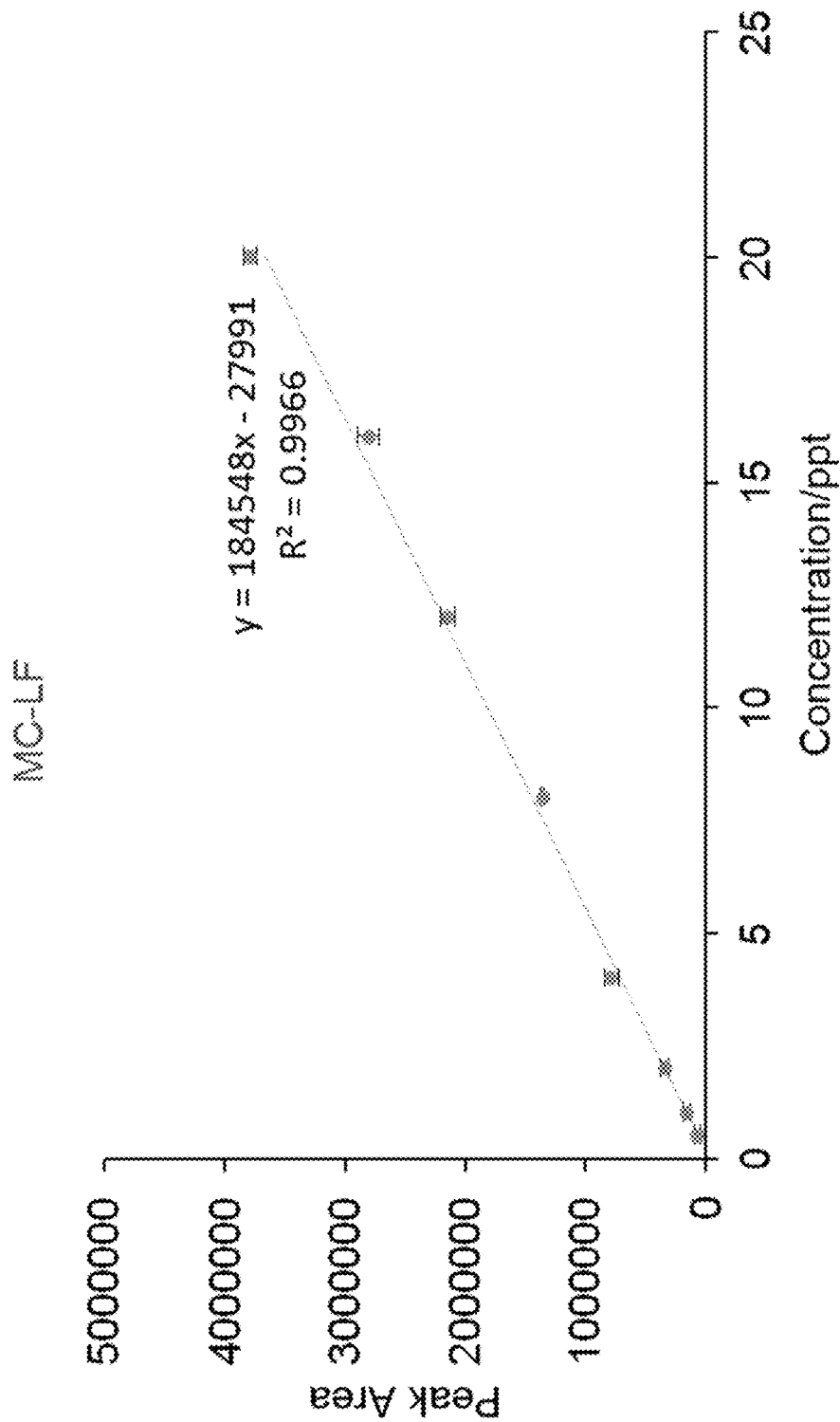
Figure 17E:
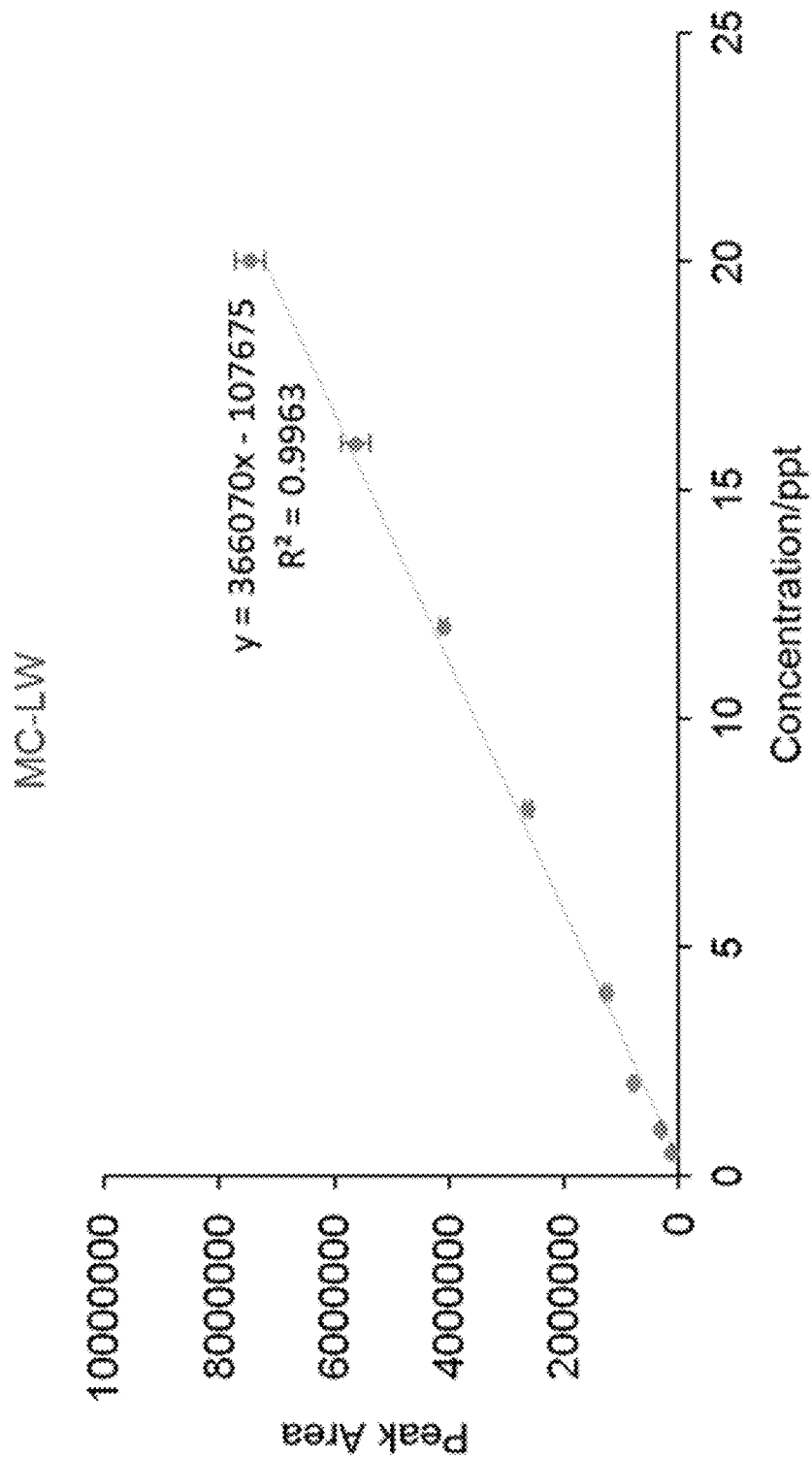
Figure 17F:
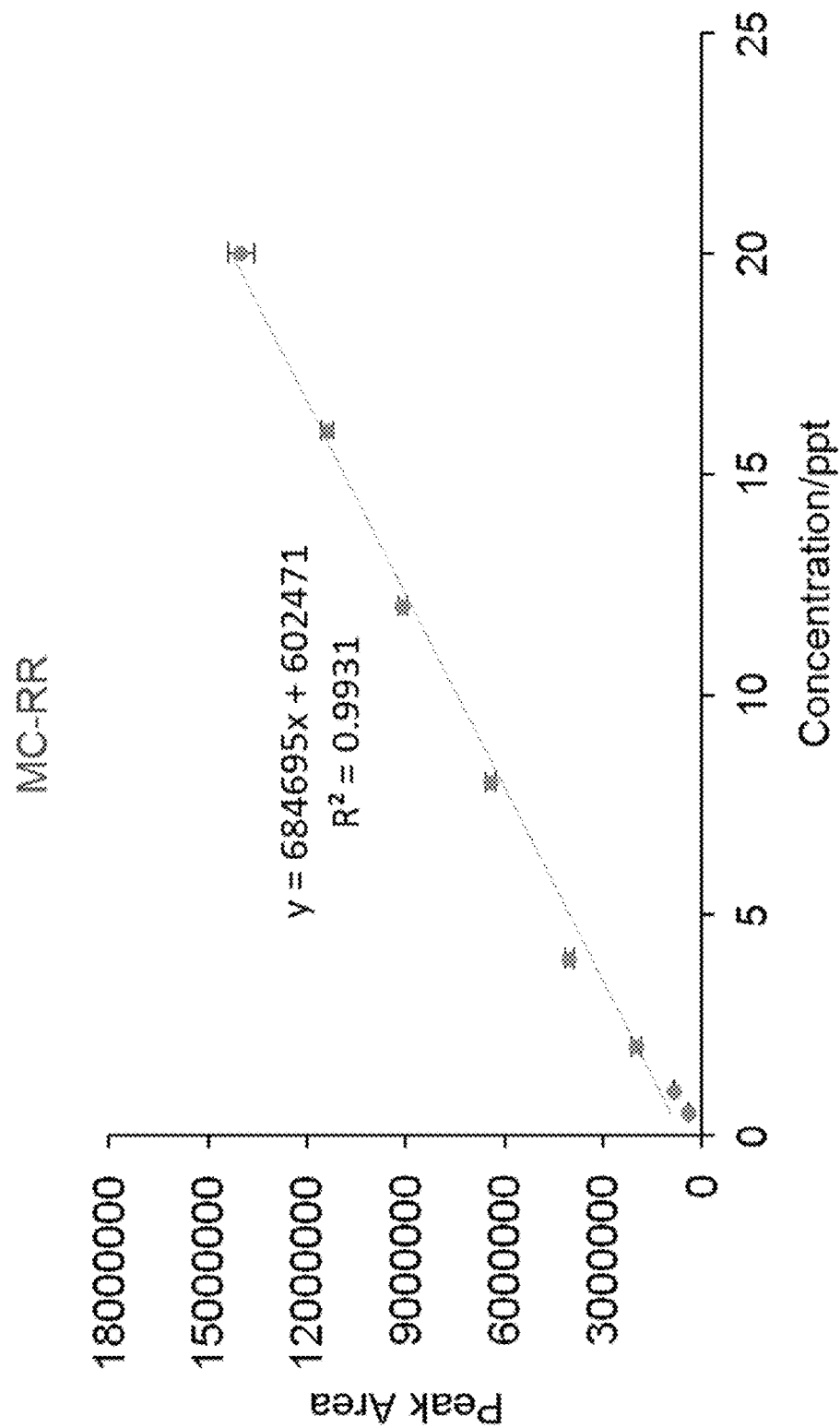

FIG. 14: Extracted ion chromatograms for a mixture of MCs.

FIGS. 15A-15F: Calibration curves without preconcentration for MC-LR (FIG. 15A), MC-LA (FIG. 15B), MC-YR (FIG. 15C), MC-LW (FIG. 15D), MC-LF (FIG. 15E), and MC-RR (FIG. 15F) in HPLC-grade water. The LOQ ranged from 25 ppt to 1 ppb without preconcentration.

FIG. 16: Table 5, displaying solid phase extraction recovery data using one SPE cartridge for a mixture containing the MC species MC-LR, MC-LA, MC-LW, MC-RR, MC-YR, and MC-LF in HPLC-grade water.

FIGS. 17A-17F: Calibration curves with preconcentration MC-LR (FIG. 17A), MC-LA (FIG. 17B), MC-YR (FIG. 17C), MC-LW (FIG. 17D), MC-LF (FIG. 17E), and MC-RR (FIG. 17F) in HPLC-grade water. The LOQ ranged from 500 ppq to 20 ppt with preconcentration.

Figure 18:
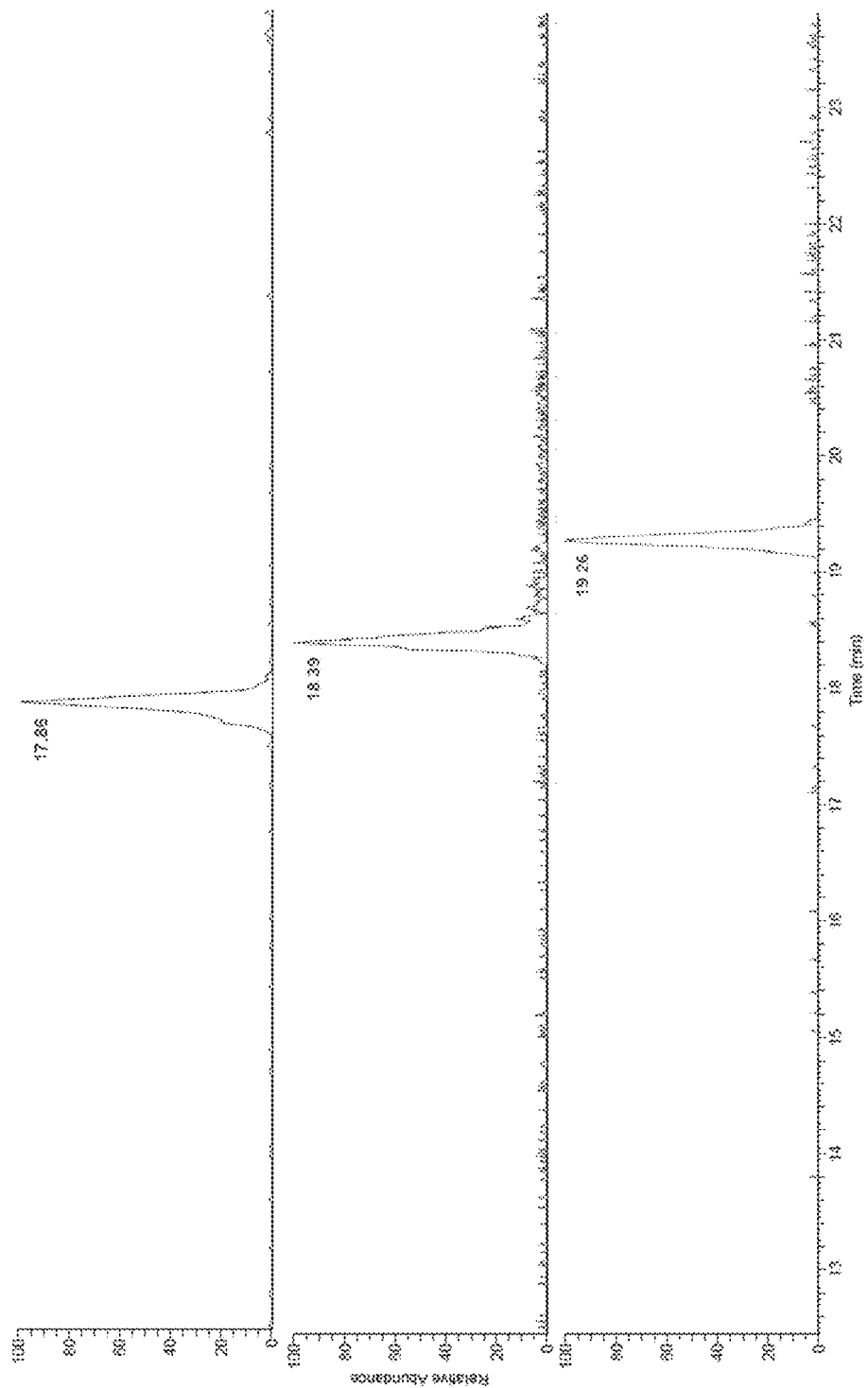

FIG. 18: EICs of doubly-charged MC-RR (top) and singly-charged MC-LR (middle) and MC-LA (bottom) ions with m/z values of 519.79, 995.56, and 910.49, respectively. Each MC was analyzed by LC-ESI-MS individually.

Figure 19A:
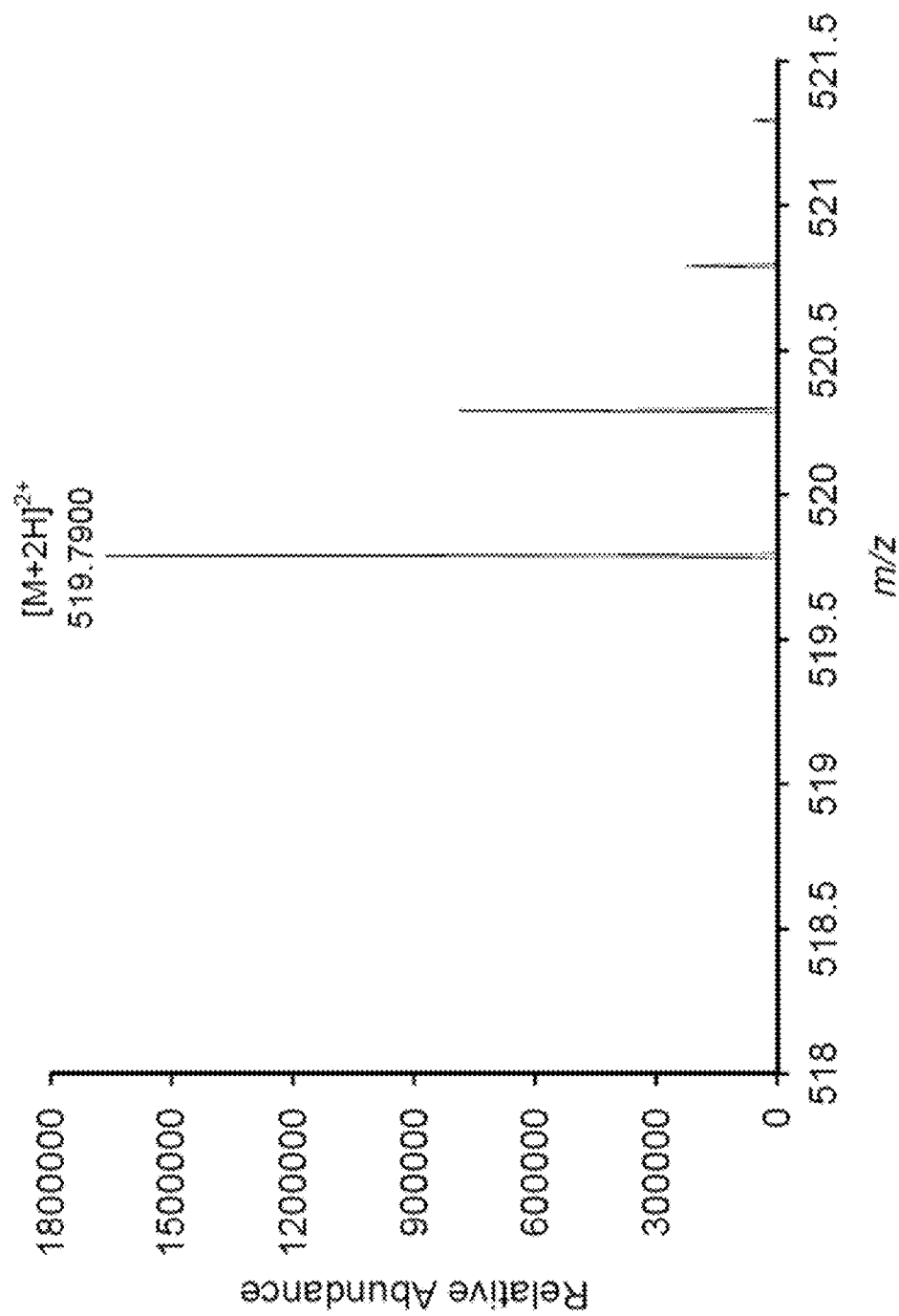
Figure 19B:
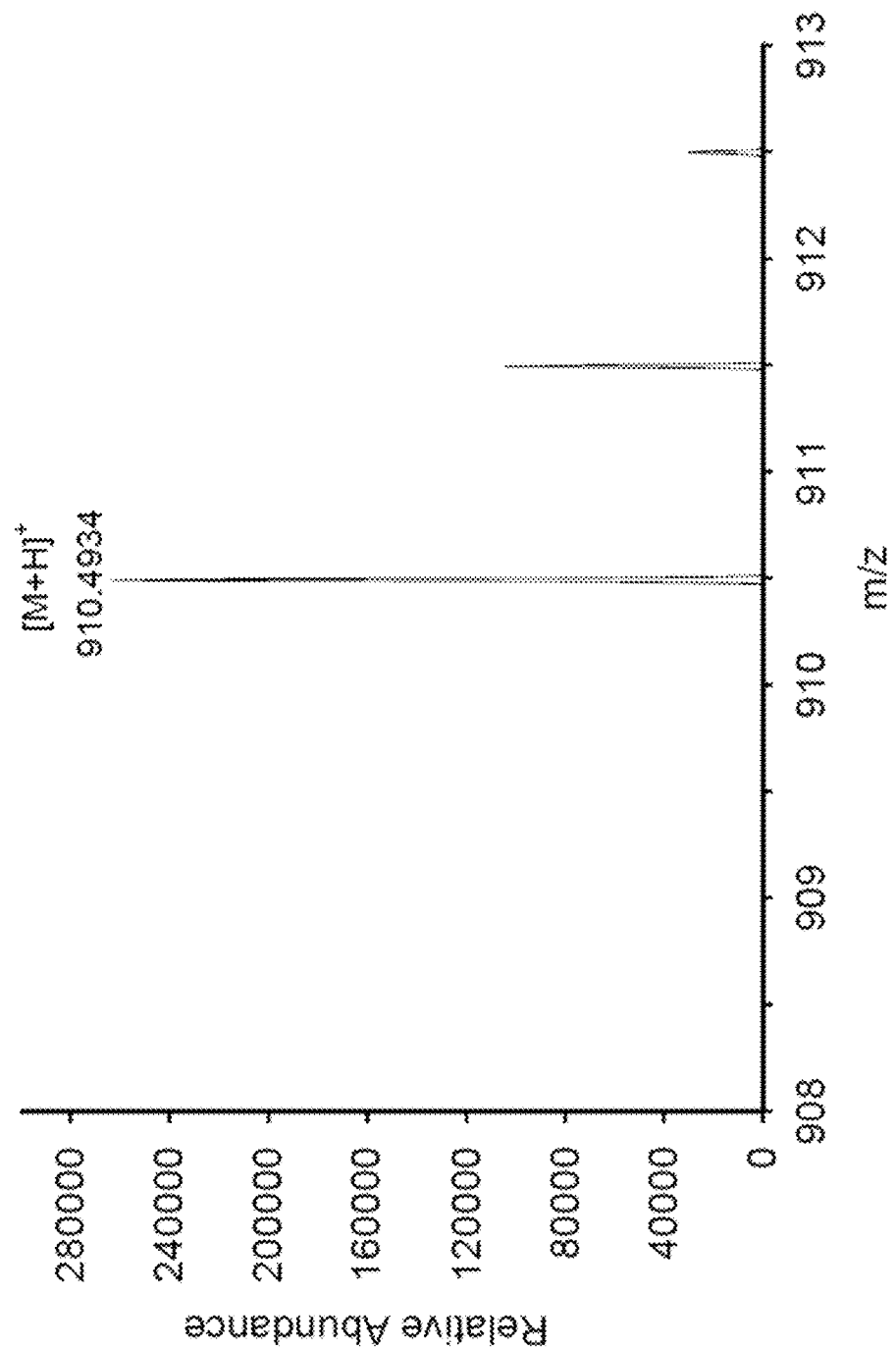

FIGS. 19A-19B: Mass spectra of doubly-charged MC-RR ion (FIG. 19A) and singly-charged MC-LA ion (FIG. 19B).

FIG. 20: Table 6, showing a comparison of LODs and LOQs of MC-LR obtained by different LC-ESI-MS and LC-ESI-MS/MS methods.

DETAILED DESCRIPTION OF THE INVENTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

For convenience, various terms are defined before further description of the present disclosure.

The terms "limit of quantification", "quantification limit", or "LOQ" refer to the lowest concentration of an analyte which can be quantitatively determined with suitable precision and accuracy (i.e., at which the performance of a method or measurement system is acceptable for a specified use).

The terms "limit of detection", "detection limit", or "LOD" refer to the lowest quantity of a substance that can be distinguished from the absence of that substance within a certain confidence limit, but not necessarily quantitated as an exact value. A detection limit is generally determined by the analysis of samples with known concentrations of analyte and by establishing the minimum level at which the analyte can be reliably detected.

The acronym "LC" refers to liquid chromatography. The acronym "ESI" refers to electrospray ionization. The acronym "MS" refers to mass spectrometry. Thus, the term "LC-MS" refers to liquid chromatography-mass spectrometry, and the term "LC-ESI-MS" refers to liquid chromatography-electrospray ionization mass spectrometry.

The acronym "SIM" refers to selected-ion monitoring, which is a mode of operation for mass spectrometers wherein only one or more selected mass-to-charge ratios (m/z values) are detected in the analysis. Thus, the term "SIM-MS" refers to a mass spectrometry analysis wherein only one or more selected m/z values are detected in the analysis. Similarly, the term "LC-SIM-MS" refers to a liquid chromatography-mass spectrometry technique wherein only one or more selected m/z values are detected in the analysis.

The term "MS/MS" refers to a mass spectrometry technique that uses two mass analyzers in tandem with a collision gas cell between the two mass analyzers. Precursor ions selected by the first mass analyzer collide with a high pressure gas in the cell and undergo fragmentation, resulting in daughter ions that are analyzed by the second mass analyzer. Thus, the term "ESI-MS/MS" refers to electrospray mass spectrometry with two mass analyzers in tandem, and the term "LC-ESI-MS/MS" refers to liquid chromatography-electrospray mass spectrometry with two mass analyzers in tandem.

Though various solvent concentrations are described for exemplary purposes, it is understood that some modifications to these concentrations are entirely encompassed within the scope of the present disclosure. For example, where 0.1% formic acid is described, it is understood that 0.05% formic acid, or 0.2% formic acid, or 1.5% formic acid could also be used to obtain similar, though perhaps not optimal, results. Similarly, where 90% acetonitrile or 90% methanol are described, it is understood that these solvents could be utilized in the same manner at concentrations of, for example, 85% or 95%, and similar though perhaps not optimal results would be obtained.

Provided herein are methods for the quantification of one or more microcystin compounds using LC-MS or LC-MS/MS, along with an optional solid phase extraction (SPE) preconcentration procedure beforehand. Structural characterization and quantification of MCs by orbitrap mass spectrometers indicates that high mass accuracy of these instruments can be beneficial for LC-MS and LC-MS/MS analyses of MC-LR. Thus, the method herein utilizes an orbitrap mass spectrometer, as will be explained in more detail.

In accordance with the present disclosure, a reproducible and efficient solid-phase extraction (SPE) method is provided for the purification and high-recovery preconcentration of MC-LR. Additionally, an LC-ESI-MS method using an HPLC orbitrap fusion MS system is provided for the accurate quantification of MC-LR. Together, the SPE method and the HPLC Orbitrap Fusion MS quantification yield a significantly improved ability to detect and quantify MCs. Moreover, provided is a method for separating a mixture of multiple MCs, and detecting each of at least six different MC species with a low LOQ.

In one aspect, the method for detecting and quantifying microcystin generally involves a SPE purification and preconcentration method, and a quantitative analysis step. The SPE purification and preconcentration method includes the steps of conditioning an SPE cartridge, equilibrating the cartridge, loading samples, desalting the loaded samples, and eluting the sample. The method may also include evaporating solvent from the eluted sample, and then redissolving the sample in a solvent. However, the desalting step is optional. The purpose of the desalting step is to remove salts and other impurities that would interfere with further analysis. Thus, the desalting step may be omitted, such as when ultrapure solvents are used for preparing the samples. However, the desalting step is particularly advantageous when natural water sources, such as lake water or river water, are being analyzed, because of the high amounts of impurities generally found in such water. Therefore, the desalting step is important for analyses of microcystins in complex (e.g., environmental) water samples.

In one non-limiting example, the conditioning step involves 3 mL of 90/10 methanol/water with 0.1% formic acid. In one non-limiting example, the equilibration step involves 2 mL of 0.1% formic acid in water. In one non-limiting example, the loading step involves loading 5 mL of samples in water. In one non-limiting example, the desalting step involves washing the samples with 1 mL of 0.1% formic acid in water. In one non-limiting example, the eluting step involves washing the cartridge with 1.5 mL of 90/10 acetonitrile/water with 0.1% formic acid. In some embodiments, the SPE cartridge is a C18 cartridge. Without wishing to be bound by theory, it is believed that the eluting step involving acetonitrile is particularly advantageous for the preconcentration of microcystins because acetonitrile is effective for the elution of peptides from SPE cartridges. Overall, the SPE purification and preconcentration of microcystins demonstrates excellent recoveries of MC-LR from dilute samples.

Following preconcentration, the quantitative analysis step generally involves LC/ESI-MS analysis with a high-resolution Orbitrap Fusion mass spectrometer. An HPLC is coupled to a high-resolution orbitrap fusion mass spectrometer to perform targeted LC-MS and LC-MS/MS quantifications of microcystins. The term "Orbitrap Fusion mass spectrometer" is used herein to generically describe a mass spectrometer that combines an orbitrap mass analyzer with a quadrupole and a linear ion trap. An orbitrap mass analyzer is one in which ions combine rotation around an electrode system with harmonic oscillations along the axis of rotation at a frequency characteristic of their mass-to-charge (m/z) ratio. A time-domain signal is collected from coherently oscillating ions, and a Fourier transform of this signal provides a mass spectrum. Thus, an orbitrap mass analyzer is a type of Fourier transform mass analyzer. A quadrupole is a component of a mass analyzer that filters sample ions based on the stability of their trajectories in oscillating electric fields that are applied to four parallel, metals rods. A linear ion trap is one in which ions are confined radially by a two-dimensional radio frequency (RF) field, and axially by stopping potentials applied to end electrodes. The term "high-resolution" means the m/z for each ion is measured to several decimal places. The combination of these features results in a mass spectrometer that provides superior results in quantifying microcystins.

Calibration curves can be constructed to quantify the MCs in a mixture. A calibration curve is a commonly used approach for determining the concentration of a substance in an unknown sample by comparing the unknown to a set of standard samples of known concentration. Without preconcentration, the method herein can result in quantification of MCs ranging from 25 ppt (LOQ) to 1 ppb or more. With preconcentration, the method herein can quantify MCs in the concentration range from 500 ppq (LOQ) to 20 ppt or more. The LOQs of MCs of 25 ppt (25 ng/L) without preconcentration, and 500 ppq (500 pg/L) with preconcentration, are among the lowest achieved using LC-MS. Thus, the method provided herein represents a substantial improvement over known methods.

Further provided is a liquid chromatography method to separate and quantify multiple MCs in a mixture. High-performance liquid chromatography (HPLC) is a separation method that uses pumps to pass a pressurized liquid solvent containing the sample mixture (referred to as the mobile phase) through a column filled with a solid adsorbent material (referred to as the stationary phase). Each component in the sample interacts differently with the adsorbent material, causing different flow rates for the different compounds and thereby leading to the separation of the components as they flow out of the column. The sample mixture is introduced into the mobile phase in the column, and the components of the sample then move through the column at different velocities, which are a function of each component's physical interactions with the adsorbent material. The time at which a specific analyte emerges from the column is known as the retention time of the analyte.

Gradient HPLC involves altering the mobile phase composition during the analysis. Gradient HPLC generally utilizes an initial mobile phase composition that is selected such that the strength is appropriate to retain and resolve early-eluting analytes, the elution strength is increased in a predetermined way to elute compounds with optimum resolution, and the final mobile phase composition is chosen to ensure elution of all compounds of interest from the column within a reasonable time. Typically, two solvents are used, and are referred to as solvents A and B. Solvent A is usually the weaker solvent, and solvent B is usually the stronger solvent. The elution strength usually increases with time. The mixing of the two mobile phases is achieved using HPLC pumps, either at low pressure, in which the solvents are proportioned on the low-pressure side of the pump using solenoid valves, or at high pressure, where two or more pumps are used to deliver the solvents at different flow rates into a mixing chamber. As the mobile phase strength increases, the analyte begins to partition into the mobile phase and move along the column. As the mobile phase strength is increasing continuously, the rate at which the analyte moves along the column accelerates. At a certain point within the column elution, the analyte may be wholly partitioned into the mobile phase, and may be moving with the same linear velocity as the mobile phase.

Provided herein is an HPLC method for the separation of multiple microcystin species in a sample. The HPLC method involves a gradient. Two pumps are utilized to produce a gradient that can separate multiple MC species in a mixture. For example, the liquid chromatography gradient can separate MC-LR, MC-YR, MC-RR, MC-LF, MC-LW, and MC-LA in a mixture. These six microcystin species are some of the most toxic and most common microcystins. To create the gradient mobile phase, a pump A pumps a solvent A, and a pump B pumps a solvent B. In some embodiment, solvent B is acetonitrile, and solvent A is 0.1% formic acid. In other embodiments, solvent B is 10% methanol with 0.1% formic acid, and solvent A is 0.1% formic acid with 20 mM ammonium formate. In one non-limiting example, the method involves the solvents acetonitrile in pump B and 0.1% formic acid in pump A, with the times and solvent parameters shown in Table 4 (FIG. 13A). This gradient curve is shown in FIG. 13B. In this example, the gradient mobile phase is created over 18 minutes by a solvent profile of 10% acetonitrile for minutes 0-2, 60% acetonitrile for minutes 2-7, 70% acetonitrile for minutes 7-12, 90% acetonitrile for minutes 12-14, and 10% acetonitrile for minutes 14-18. In another non-limiting example, the gradient mobile phase is created over 30 minutes by a solvent profile of 10% methanol with 0.1% formic acid for minutes 0-2, 80% methanol with 0.1% formic acid for minutes 2-16, 90% methanol with 0.1% formic acid for minutes 16-22, and 10% methanol with 0.1% formic acid for minutes 22-30.

The methods described herein are useful for analyzing microcystin content in dilute aqueous samples. The methods are particularly useful for the analysis of water samples from lakes, rivers, streams, and ponds. The methods are also particularly useful for testing tap water samples to ensure the safety of drinking water. The sample can contain a plurality of microcystin species, which can be separated and quantified as described herein. The methods provided herein are capable of efficiently quantifying high-pg/L (ppq) concentrations of microcystin compounds by LC-MS after preconcentration, and ng/L (ppt) concentrations of microcystin compounds by LC-SIM-MS and LC-MS/MS without preconcentration. The methods provide limits of quantification (LOQs) and recoveries of MC-LR that are drastically improved over known methods.

It is further envisioned that the methods described herein may be embodied in the form of a kit or kits, such as a kit for the detection and quantification of microcystins in drinking water. Such a kit may include, for example, two or more of the SPE cartridges and solvents described herein, in separate containers, where the containers may or may not be present in a combined configuration. Many other kits are possible, such as kits further comprising one or more standard solutions for reference purposes, and kits including 96-well plates for high-throughput sample preparation and analyses, in which case multiple microcystins can be simultaneously purified and preconcentrated using SPE and sequentially analyzed by LC-MS using an autosampler. The kits may further include instructions for using the components of the kit to practice the subject methods. The instructions may describe, for example, a particular HPLC gradient useful for separating multiple microcystin species, and may further include example calibration curves. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1

This example describes how an HPLC was coupled to an orbitrap fusion mass spectrometer to separate, identify, and quantify MC-LR at low concentration levels using high-mass accuracy, SIM-MS, and MS/MS capabilities of this instrument. The ng/L concentrations of MC-LR in water were quantified by LC-SIM-MS and LC-MS/MS. The LOQ of MC-LR was improved to pg/L levels by the development of an efficient SPE method for the recovery and preconcentration of MC-LR. Thus, this example demonstrates that the methods provided herein can be applied to efficiently and reproducibly preconcentrate, separate, and quantify MC-LR by a LC-orbitrap-MS system.

A high-performance liquid chromatography-electrospray ionization mass spectrometry (HPLC-ESI-MS) method was utilized for the quantification of the cyanobacterial toxin microcystin-LR (MC-LR) in water and in the aqueous solutions containing MC-LR, MC-LA, and MC-RR. While an HPLC binary gradient was applied for the separation of MCs in aqueous solutions and tap water, quantification of singly-charged MC-LR ion (m/z 995.56, z=+1) was achieved in selected ion monitoring (SIM) mode using an Orbitrap Fusion Tribrid mass spectrometer. All MC ions were detected with high mass accuracy of <3 parts per million (ppm) using the orbitrap mass analyzer and MC-LR was quantified using external calibration based on ion intensities. Calibration curves were linear, and limits of quantifications (LOQs) of MC-LR by LC-SIM-MS were 25 ng/L without preconcentration and 500 pg/L after MC-LR preconcentration. The percent recoveries of MC-LR after solid phase extraction (SPE) and sample preconcentration were in the range from 98.35% to 99.85% with a relative standard deviation (RSD) of <3%, indicating that this is one of the most efficient and reproducible SPE methods for MC-LR recovery. Additionally, a LC-tandem mass spectrometry (MS/MS) method based on the measurement of the intensity of a characteristic MC-LR fragment ion (m/z 135.08) was established for quantification of MC-LR. Overall, MC-LR recovery and preconcentration method developed and LC-SIM-MS enable sensitive, selective, and reproducible quantification of MC-LR using MS and MS/MS capabilities of a high-mass accuracy orbitrap mass spectrometer.

Sample Preparation and Preconcentration

For sample preparation and preconcentration, MC-LR standards were made from a 500 ppm stock solution that was prepared by ethanol by the manufacturer. Other standard concentrations were prepared by diluting the 500 ppm stock in 90:10 (v:v) $CH_3OH:H_2O$ (HPLC-grade solvents). Initially, MC-LR standard samples were analyzed by LC-ESI-MS without preconcentration. In order to improve quantification limits, samples were preconcentrated using solid-phase extraction (SPE) before LC-MS analysis. SPE was performed using Sep-Pak C18 plus light cartridges (Waters). The cartridges were conditioned with 3 mL of 90:10 (v:v) $CH_3OH:H_2O$ with 0.1% FA and then equilibrated with 2 mL of 0.1% FA. The MC-LR sample was then diluted to 5 mL with water and loaded onto the cartridge. An optional sample desalting step was performed for the samples that were not prepared in HPLC-grade water (e.g., for tap water) by adding 1 mL of 0.1% FA onto the cartridge. The sample was then eluted and collected using 1.5 mL of 50:50 (v:v) $CH_3CN:H_2O$ containing 0.1% FA. The solvent was evaporated from the sample using a heated centrifuge at 45° C. for two hours. After evaporation, the sample was redissolved in 100 μL of 90:10 (v:v) $CH_3OH:H_2O$ containing 0.1% FA.

LC-ESI-ME Method

The HPLC method used was Method 544 developed by the EPA with various modifications. A selected ion monitoring (SIM) method (Thermo) was optimized for identification and quantification of MC-LR using Orbitrap Fusion-MS. SIM scans were set up for the singly-charged MC-LR ion (m/z 995.56), which were isolated using the quadrupole and an isolation width of 5 m/z units. The ions were detected using the orbitrap mass analyzer with the orbitrap resolution set to 120,000. External calibration curves were constructed to quantify MC-LR samples by analyzing standard MC-LR samples with concentrations from ~10 ppt-10 ppb (no sample preconcentration) and ~500 ppq-35 ppt (for preconcentrated samples).

Determination of SPE Preconcentration Recovery 1.25 ppb solution of MC-LR was prepared in 90:10 (v:v) $CH_3OH:H_2O$ by diluting a 500 ppm MC-LR stock solution. 100 µL of the 1.25 ppb MC-LR solution was transferred into a glass vial and diluted 50× to a final volume of 5.00 mL with HPLC-grade water (the after-dilution concentration of MC-LR was 25 ppt). The SPE protocol described above was used for the preconcentration experiments. To ensure that the results were reproducible from one cartridge to the next, each experiment was performed with three different SPE cartridges. Quantification of MC-LR eluted from each of the three SPE cartridges was performed by LC-ESI-MS in triplicate, and the percent recovery was calculated and averaged for MC-LR samples eluted from the three cartridges. The preconcentration procedure was also performed using an MC-LR sample with initial concentration of 750 ppt to ensure that the procedure was reproducible and efficient for samples containing lower concentrations of MC-LR. The limit of quantification (LOQ) of MC-LR in water samples that were not preconcentrated was ~10 ppt, which is comparable to the LOQ obtained using other similar instruments previously. The SPE method enabled high-recovery (>98%) preconcentration of MC-LR before LC-MS analyses. The recovery was better than reported in the literature (e.g., recovery ranged from ~82.4-117% in EPA method 544). The preconcentration improved the LOQ of MC-LR to ~500 ppq. Altogether, this example shows that the high-recovery SPE preconcentration method and LC-MS method characterized with high mass resolution, accuracy, and reproducibility, is useful for the detection of microcystin in water (e.g., in water plants), and is also useful in more complex samples (e.g., in environmental water samples).

Materials and Reagents

HPLC-grade acetonitrile ($CH_3CN$), methanol ($CH_3OH$), and water ($H_2O$) were obtained from Fisher Scientific (Pittsburgh, Pa., USA). Reagent-grade (≥95%) formic acid (FA) and ammonium formate were purchased from Sigma (St. Louis, Mo., USA). The stock solutions of 110 500 mg/L of MC-LR, 500 mg/L of MC-LA, and 100 mg/L of MC-RR prepared by the manufacturer in ethanol were purchased from Cayman Chemical Company (Ann Arbor, Mich., USA). Sep-Pak C18 Plus Light Cartridges were purchased from Waters (Milford, Mass., USA). Cellulose acetate membrane filters (0.2 m pore size) were purchased from Fisher Scientific (Swedesboro, N.J., USA). 3 mL and 10 mL syringes were obtained from Becton, Dickinson and Company (Franklin Lakes, N.J., USA). 2 mL clear glass vials were purchased from Restek (Bellefonte, Pa., USA). The heated vacuum concentrator was from Eppendorf (Hamburg, Germany).

Standard Solution Preparation and SPE Protocol

MC-LR standards and blind standards were prepared by diluting the 500 mg/L stock solution using $CH_3OH:H_2O$ (90:10, v/v). Initially, MC-LR standard samples were analyzed by LC-ESI-MS without preconcentration. In order to improve the LOQ of MC-LR, the samples were purified using SPE and then preconcentrated before LC-MS analysis. The SPE cartridges were conditioned with 3 mL of $CH_3OH:H_2O$ (90:10, v/v) containing 0.1% FA and then equilibrated with 2 mL of 0.1% FA. The dilute aqueous solution containing MC-LR was loaded onto the SPE cartridge, although loading volume can be adjusted as needed. For the complex samples, such as tap water and river water, an optional washing step was performed after the loading step by adding 1 mL of 0.1% FA onto the cartridge. The sample was then eluted using 1.5 mL of $CH_3CN:H_2O$ (50:50, v/v) containing 0.1% FA, and collected in a glass vial. The sample was then preconcentrated by evaporating the solvent using a heated vacuum concentrator, and redissolved in a desired volume of $CH_3OH:H_2O$ (90:10, v/v) containing 0.1% FA before LC-MS analysis.

LC-MS

Initially, the HPLC (Shimadzu Technologies, Addison, Ill.) consisted of two LC-20AD pumps, DGU-20A3 degasser, a manual injector, and SCL-10A VP system controller. A CBM-20A system controller and an autosampler SIL-20A HT were then integrated into HPLC system to perform sequential automated injections of MC samples. Separation of MC-LR was performed on a 3.0 mm (i. d.)×100 mm (length) XBridge C8 column (Waters) packed with 3.5 µm-diameter C8 solid phase particles. HPLC binary gradient was established. The solvent flow rate was 0.3 mL/min and the sample injection volume was 20 µL. Mobile phase A consisted of water containing 0.1% FA and 20 mM ammonium formate while mobile phase B was methanol containing 0.1% FA. The gradient that was used for the separation and detection of MC-LR was 0-2 min 10% of B, 2-16 min 80% of B, 16-22 min 90% of B, 22-30 min 10% of B, and the run was stopped at 30 min.

For detection and quantification of MC-LR, the HPLC was coupled to an Orbitrap Fusion (Thermo Scientific, San Jose, Calif.) mass spectrometer, which contains a quadrupole, a linear ion trap, and an orbitrap mass analyzer. MS data were acquired using Xcalibur software (Thermo Scientific). The ESI-MS experiments were performed in positive ion mode using a heated ESI (HESI) source. Orbitrap mass analyzer was calibrated in the m/z range 100-2000 using a standard calibration mixture containing n-butylamine, caffeine, the peptide MRFA, and the synthetic polymer Ultramark 1621 (Thermo). A syringe pump (Chymex Inc, Stafford, Tex., USA) was used for direct sample infusion to optimize the HESI source conditions and instrument parameters prior to LC-MS. The spray voltage was 2400 V, sheath gas (nitrogen) flow rate was 35 arbitrary units (~4.1 µL/min), auxiliary gas (nitrogen) flow rate was 10 arbitrary units (~8.0 L/min), ion transfer tube temperature was 325° C., and the vaporizer temperature was 285° C.

LC-ESI-MS and LC-ESI-MS/MS Quantification of MC-LR

The Orbitrap Fusion MS method was designed so that LC-SIM-MS and MS/MS scans were performed for the quantification of MC-LR during the same run for each sample. LC-SIM-MS utilized quadrupole to isolate singly-charged MC-LR ion (m/z 995.56) with an isolation width of 5 m/z units. Singly-charged protonated ions of MC-LA (m/z 910.49) and MC-RR (m/z 1038.57) were analyzed by LC-SIM-MS separately from MC-LR using also quadrupole isolation width of 5 m/z units. The intensity threshold was set to $1.0\times10^3$ with mass tolerance of 10 ppm. MC ions were detected using the orbitrap mass analyzer with the orbitrap resolution set to 120,000. The automatic gain control (AGC) target was $5.0\times10^4$ with the maximum injection time of 100 ms.

For quantification of MC-LR by LC-MS/MS, the precursor MC-LR ion (m/z 995.56) was selected by the quadrupole using an isolation window of 1.6 m/z units, and fragmented by higher-energy collisional dissociation (HCD) in the ion-routing multipole. MC-LR fragments were obtained using HCD collision energy of 45%, and the AGC target was set to $5.0\times10^4$ with the maximum injection time of 60 ms. Fragment ions were detected in the orbitrap mass analyzer with the orbitrap resolution set to 30,000. All samples were analyzed by LC-SIM-MS and LC-MS/MS in triplicate. The Qual Browser of Xcalibur software was used to display mass spectra and find ion intensities. Extracted ion chromatograms (EICs) were obtained using Xcalibur Quan Browser and displayed in the figures after performing a 5-point smoothing.

Quantification of MC-LR in Blind Standards and Tap Water

Two blind standards containing 2.00 µg/L and 22.50 ng/L of MC-LR were prepared, and the latter sample was purified by SPE and preconcentrated 50× before LC-MS analysis using the procedure described above. A sample of tap water (4.90 mL) was spiked with 100 µL of 1.25 µg/L solution of MC-LR yielding 25.00 ng/L solution of MC-LR, which was then purified by SPE and preconcentrated. The solutions of 3 µg/L MC-LR, 3 µg/L MC-LA, and 30 µg/L MC-RR were prepared by diluting MC stock solutions with $CH_3OH:H_2O$ (90:10, v/v). 100 µl of each of the three MC solutions was transferred into a 2 mL glass vial to prepare the sample containing 1 µg/L of MC-LR, 1 µg/L of MC-LA, and 10 µg/L of MC-RR. MC-LR in all of these samples was then quantified by LC-ESI-SIM-MS.

Quantification of MC-LR in Blind Samples and a Mixture with Other MCs by LC-ESI-MS A calibration curve was constructed by analyzing standard solutions in triplicate at eight concentration levels between 25 ng/L and 10 µg/L for the quantification of MC-LR in spiked HPLC-grade water samples. Blind samples containing 2.00 µg/L of MC-LR was prepared to validate the calibration curve.

The calibration curve was then applied to quantify MC-LR in a mixture with MC-LA and MC-RR. The solutions of 3 µg/L MC-1R, 3 µg/L MC-LA, and 3 µg/L MC-RR were prepared by diluting MC stock solutions with $CH_3OH:H_2O$ (90:10 v/v). 100 µl of each of the three MC solutions was transferred into a 2 mL glass vial to prepare the sample containing 1 µg/L of MC-LR, MC-LA, and MC-RR. MC-LR was then quantified by LC-ESI-SIM-MS.

Determination of Percent Recovery of MC-LR Using SPE

The percent recovery of the MC-LR was tested in HPLC-grade water and river water spiked with MC-LR. River water was collected from the Ottawa river (Toledo, Ohio, USA). River water was filtered through a cellulose membrane with a pore size of 0.20 m.

The percent recovery was determined by spiking 1.25 µg/L and 750 ng/L solutions of MC-LR into HPLC-grade water and river water followed by using three C18 SPE cartridges for each concentration. The samples of MC-LR with concentrations of 1.25 µg/L and 750 ng/L were prepared by diluting 500 mg/L MC-LR stock solution in $CH_3OH:H_2O$ (90:10 v/v). Then, 100 µL of each solution (1.25 µg/L and 750 ng/L) was transferred into glass vials and diluted to a final volume of 5 mL with HPLC-grade or river water yielding 25 ng/L and 15 ng/L solutions of MC-LR, respectively. Three SPEs were performed for each concentration for both HPLC-grade water and river water samples as described in the SPE protocol. An additional washing step, also described above, was performed for the spiked river water samples to purify MC-LR further before the elution step. Each preconcentrated MC-LR sample was then redissolved in 100 L of $CH_3OH:H_2O$ (90:10 v/v) and analyzed by LC-ESI-MS in triplicate. SPE was not performed for the control MC-LR solutions (1.25 µg/L and 750 ng/L).

To determine percent recovery, the intensity of the MC-LR ion (m/z 995.56) after SPE was divided by the intensity of this ion in a control sample and averaged for each concentration separately for both MC-LR spiked HPLC-grade and river water samples.

Quantification of MC-LR in Real World Samples

An LC-MS calibration curve was prepared after purifying and preconcentrating MC-LR solutions in tap water with concentrations between 500 pg/L and 35 ng/L. To validate the calibration curve, blind standards containing 22.50 ng/L and 25.00 ng/L of MC-LR were prepared in HPLC-grade water and tap water, respectively. 100 µL of 1.125 µg/L and 1.25 µg/L solutions of MC-LR were spiked into 4.90 mL of HPLC-grade and tap water to yield 22.50 ng/L and 25 ng/L concentrations of MC-LR respectively. Blind samples were purified by SPE and preconcentrated 50× before LC-MS analysis using the procedure described above for the SPE protocol.

The SPE method was further validated by quantifying MC-LR in spiked river water. The samples of MC-LR with concentrations of 100 ng/L, 250 ng/L, 500 ng/L, and 1 µg/L were prepared by diluting a 500 mg/L MC-LR stock solution in $CH_3OH:H_2O$ (90:10, v/v). Then, 100 µL of each solution was transferred into glass vials and diluted to a final volume of 5 mL with filtered river water yielding 2 ng/L, 5 ng/L, 10 ng/L, and 20 ng/L solutions of MC-LR, respectively. SPEs of MC-LR were performed for both calibration standards and river water samples. A calibration curve for quantification of MC-LR in spiked river water samples using LC-ESI-MS was constructed at eight concentration levels between 2 ng/L and 35 ng/L.

For all samples, LODs were obtained experimentally by analyzing spiked water samples with signal-to-noise (S/N) ratio ~3 from the extracted ion chromatograms, while LOQs were estimated from the chromatograms as the lowest validated concentration level that meets a S/N ratio equal to 10.

Results and Discussion

General Considerations Regarding MS and MS/MS Method

Figure 1:
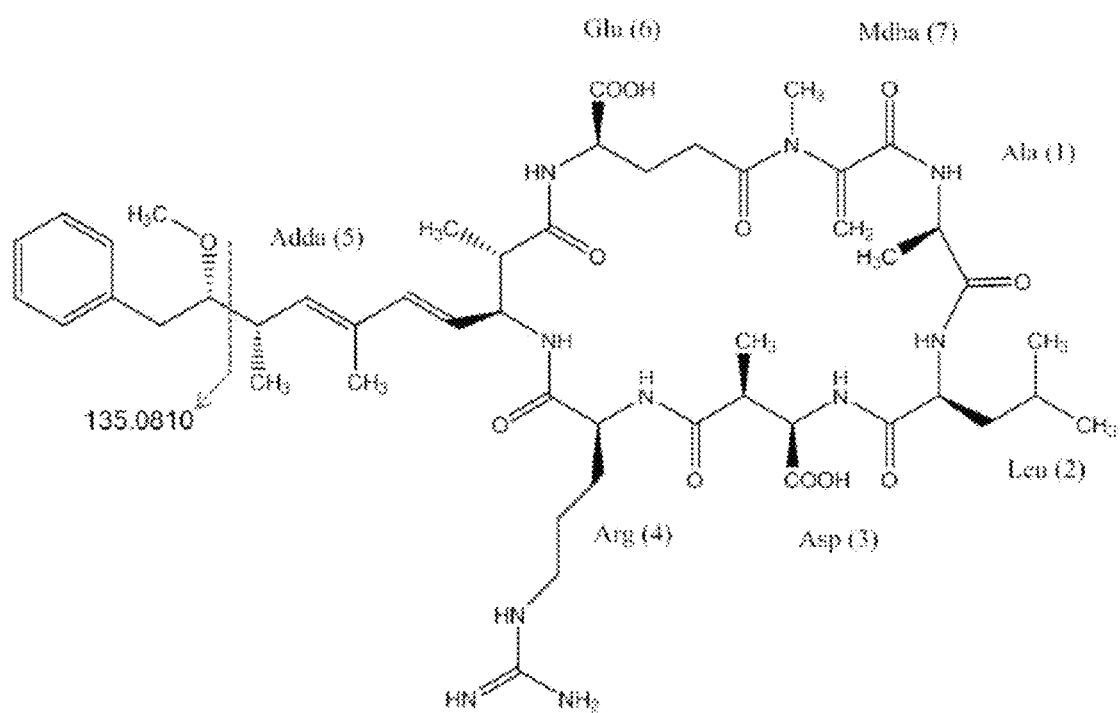

After optimizing ESI-MS detection of MC-LR using direct infusion, LC-SIM-MS analyses of MC-LR were performed. The singly-charged protonated MC-LR ion (m/z 995.56) was quantified by LC-MS in positive ion mode. SIM was chosen for the MS analyses because it enables detection and quantification of MC-LR with higher sensitivity than full MC scan. Selection of a SIM mass window was important because a narrow m/z window might result in the loss of the sensitivity, and a wide SIM range can cause interference from neighboring peaks. Therefore, a 5 m/z units window was selected using a quadrupole so that the mass range for SIM is centered at the exact precursor mass (m/z 995.56). MS and MS/MS were performed in parallel. In the SIM-MS scans, the orbitrap fusion mass spectrometer uses the quadrupole to isolate MC-LR ions, which are then stored in the IRM and injected using a C-trap into the orbitrap for mass analysis. For MS/MS, MC-LR ions were isolated within the specified mass range (1.6 m/z units), fragmented by HCD, and sent to the orbitrap for simultaneous mass analysis. Alternatively, targeted quantitation of MC-LR can be done using MS/MS in parallel to MS. ADDA fragment ion $[C_6H_5—CH_2CH(OCH_3)]^+200$ (m/z~135.0810) formed due to the cleavage of the ADDA group (FIG. 1) and was used for quantification of MC-LR by LC-MS/MS. The high-throughput analysis was feasible since both SIM-MS and MS/MS scans were performed within the same method for each sample using the Orbitrap Fusion MS.

To improve parallel MS and MS/MS data acquisition by Orbitrap Fusion MS, parameters such as mass resolution, scan rate, AGC, and maximum injection time were adjusted starting from the default values. ~4 Hz orbitrap scan rate was set to obtain relatively high resolution during SIM scan. The AGC target value controls the number of ions that the ion optics injects into the orbitrap mass analyzer. Ions will stop filling orbitrap when AGC target is reached or when maximum ion injection time expires. A higher value of AGC target increases the sensitivity, but it might cause peak broadening due to space charging in the orbitrap. AGC and maximum injection time were balanced to obtain the best MC-LR signal in the method used.

Figure 2A:
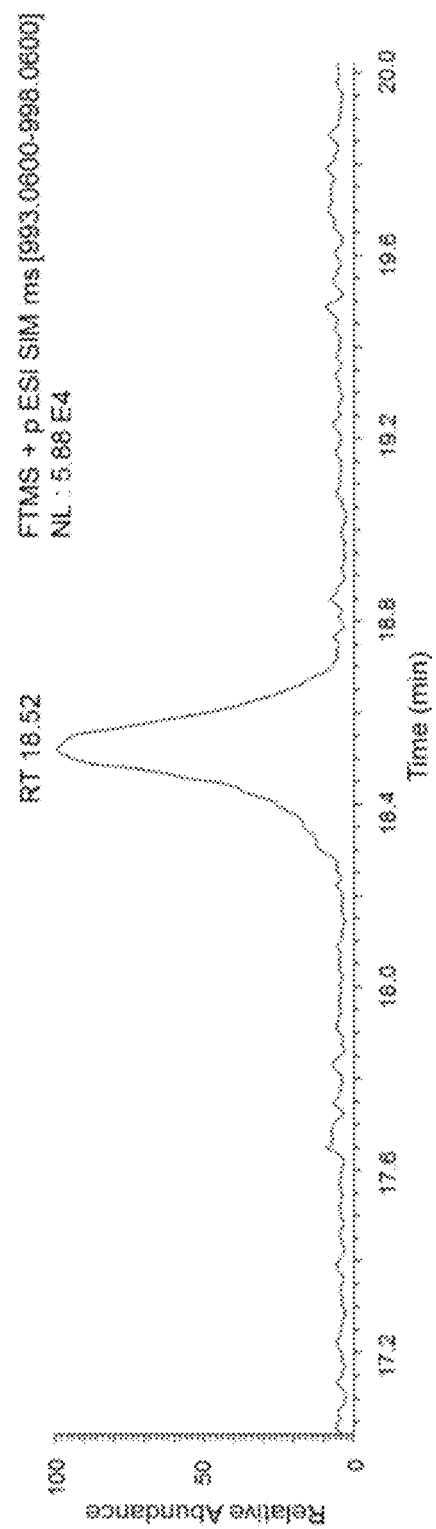
Figure 2B:
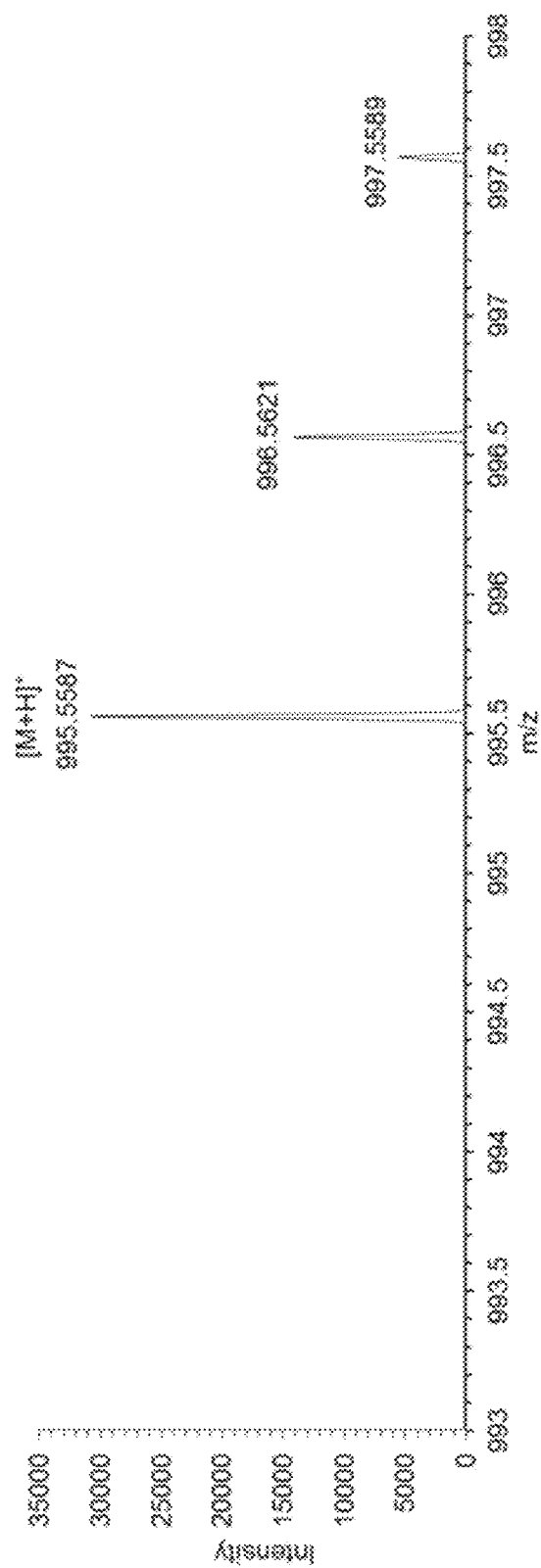

The EIC obtained upon LC-SIM-MS analysis of 1 µg/L solution of MC-LR indicates that its retention time is ~18.50 min (FIG. 2A). The ESI orbitrap mass spectrum clearly shows the monoisotopic peak of protonated MC-LR at m/z 995.5587 with other isotopic peaks resolved (FIG. 2B). Ions formed by ESI were analyzed using the orbitrap mass analyzer, which was externally calibrated to provide high-mass accuracy measurements. For example, m/z of monoisotopic MC-LR ion was measured with mass accuracy of ~2.1 ppm (Table 1), and this value falls within mass accuracy range (<3 ppm) of Orbitrap Fusion MS specified by the manufacturer (Thermo).

TABLE 1

Mass accuracies of singly-charged protonated ions of MC-LR, MC-LA, and MC-RR

| MC | Ion formula | Theoretical m/z | Experimental m/z[a] | Accuracy (ppm) |
|---|---|---|---|---|
| MC-LR | $[C_{49}H_{74}N_{10}O_{12} + H]^+$ | 995.5566 | 995.5587 | −2.1094 |
| MC-LA | $[C_{46}H_{67}N_{7}O_{12} + H]^+$ | 910.4926 | 910.4934 | −0.8786 |
| MC-RR | $[C_{49}H_{75}N_{13}O_{12} + H]^+$ | 1038.5736 | 1038.5748 | −1.1554 |

[a]Values correspond to monoisotopic peaks in mass spectra shown in FIG. 2B

Quantification of MC-LR without Preconcentration

The intensity of the ion with m/z 995.56 was used for LC-SIM-MS quantification of MC-LR in water using external calibration. The MC-LR standards were prepared, analyzed in triplicate, and the intensities were averaged to generate each point of the calibration curve shown in FIG. 3. This calibration curve was obtained for MC-LR without preconcentration over the concentration range of 25 ng/L to 10 µg/L with the standard deviations included as error bars. The calibration curve was linear with an excellent $R^2$ value of 0.9999. Lower concentrations of MC-LR can be detected (LOD~10 ng/L), but cannot be quantified using orbitrap without preconcentration of the sample prior to analysis. Without sample preconcentration, the LOQ of MC-LR by LC-SIM-MS was 25 ng/L, and the EIC and mass spectrum of MC-LR corresponding to the LOQ are shown in FIG. 4. The LOQ of MC-LR obtained using Orbitrap Fusion Tribrid MS is improved compared to the LOQs measured by other models of orbitrap mass spectrometers.

The calibration curve was validated using a blind standard, which was made by one individual and then analyzed by a different individual. After LC-SIM-MS analyses were performed, it was determined that concentration of MC-LR in the blind standard was 1.92 µg/L while the actual concentration of MC-LR was 2.00 µg/L (Table 2). The results of this experiment indicate that the quantification of MC-LR using calibration curve in FIG. 3 was accurate (4.85% RSD).

TABLE 2

Validation of calibration curves for quantification of MC-LR using LC-MS

| MC-LR sample | MC-LR concentration | Calculated concentration | RSD (%) |
|---|---|---|---|
| Analyzed without preconcentration: | | | |
| Blind standard | 2.00 µg/L | 1.92 µg/L | 4.85 |
| Mixed with MC-RR and MC-LA | 1.00 µg/L | 0.97 µg/L | 2.18 |
| Analyzed after preconcentration: | | | |
| Blind standard | 22.50 ng/L | 22.77 ng/L | 7.92 |
| Spiked in tap water | 25.00 ng/L | 25.45 ng/L | 2.21 |
| Spiked in river water | 2.00 ng/L | 1.62 ng/L | 8.11 |
| | 5.00 ng/L | 4.28 ng/L | 6.82 |
| | 10.00 ng/L | 10.35 ng/L | 3.91 |
| | 20.00 ng/L | 20.76 ng/L | 2.24 |

Figure 3:
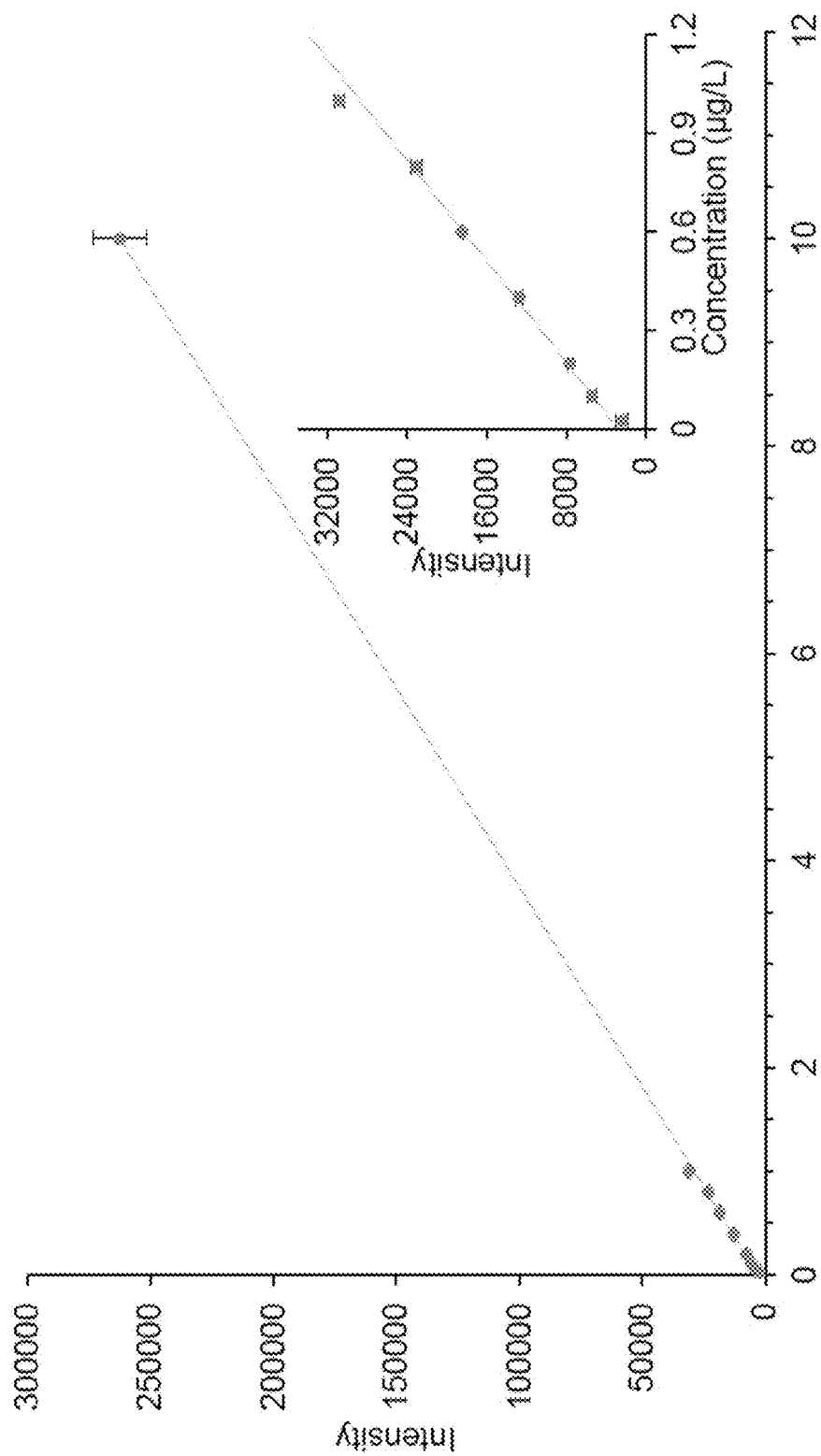
Figure 4A:
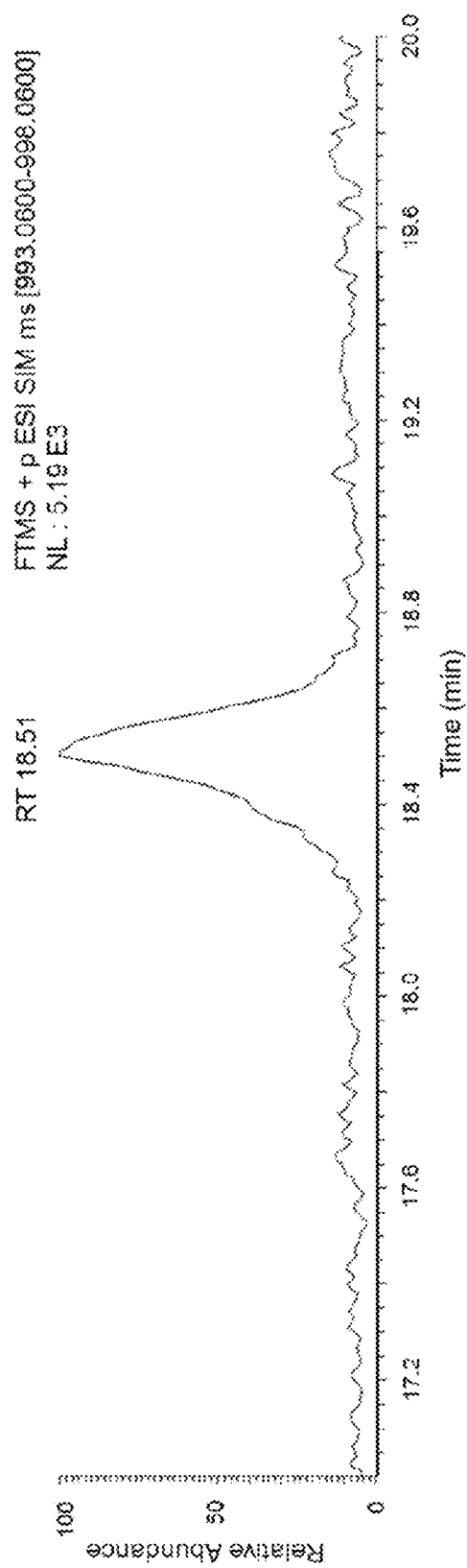
Figure 4B:
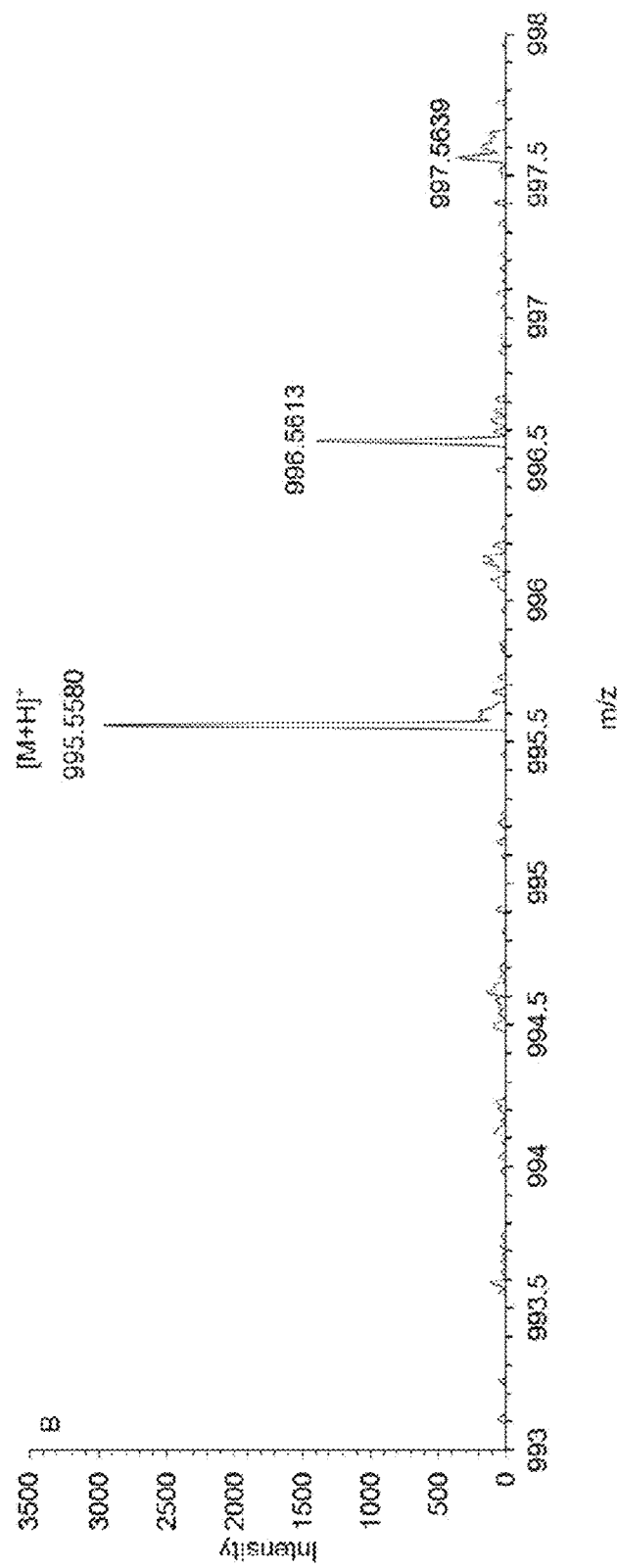

The calibration curve shown in FIG. 3 was then applied to quantify MC-LR in more complex samples. HPLC separation of MC-LR was performed in a mixture containing 1 µg/L of MC-LR, MC-LA, and MC-RR. The intensities of singly-charged MC-LR and MC-LA ions and doubly-charged MC-RR ion, whose m/z values are shown in Table 1, were monitored individually by SIM-MS. FIG. 18 shows the EICs for MC-RR ($t_R$=17.86 min), MC-LR ($t_R$=18.39 min), and MC-LA ($t_R$=19.26 min). FIGS. 19A-19B show the mass spectra of MC-LA and MC-RR, and m/z values of their singly and doubly charged ions, respectively, were measured with excellent mass accuracies <3 ppm (Table 1). Since pure stock solutions of MCs were used for preparation of the mixture, sample purification using SPE was not necessary before the LC-SIM-MS analysis. The concentration of MC-LR in the mixture with other MCs, measured using LC-SIM-MS of MC-LR ion with m/z 995.56 and the calibration curve in FIG. 3, was 0.97 µg/L (Table 2), showing 2.18% RSD in comparison to initial concentration of MC-LR (1.00 µg/L).

Quantification of MC-LR after Preconcentration

To analyze MC-LR samples of lower concentrations and higher complexity, a method for the purification of MC-LR using SPE was developed and used for the preconcentration of the sample. The accuracy and the precision of the developed SPE method were evaluated in a recovery experiment by analyzing MC-LR spiked HPLC-grade water and river water samples at two concentration levels (25 ng/L and 15 ng/L). River water was selected for the analyses to evaluate possible matrix effects on recovery of MC-LR using the developed SPE method.

MC-LR solutions were purified using C18 SPE cartridges and preconcentrated 50× as described above. The loading volume of the cartridge was kept at 5 mL, but it can be increased or decreased depending on the concentration of MC-LR in the solution. Low loading volumes minimize the sample preparation time and reduce potential losses of MC-LR in the SPE column during sample loading.

Average percent recovery was determined by comparing MS intensities of the protonated MC-LR ion (m/z 995.56) in preconcentrated samples and standard samples containing 1.25 µg/L and 750 ng/L of MC-LR (Table 3). Accuracy of the SPE method expressed as average recovery ranged from 98.35% to 99.85% and 97.55% to 98.52% for MC-LR spiked HPLC-grade water and river water, respectively, at the two concentrations. Precision of the developed SPE method expressed as RSD was calculated from three replicates on each concentration using three different SPE C18 cartridges for each water sample. In all cases, RSDs were below 3.00% for MC-LR spiked HPLC-grade water and river water samples (Table 3). RSD of the signal intensities of LC-ESI-MS trials was less than or equal to 4.68%, which shows excellent reproducibility of the MS method.

TABLE 3

Percent recovery of MC-LR after SPE purification and preconcentration of 25 ng/L and 15 ng/L solutions of MC-LR, which were preconcentrated 50× to yield ~1.25 µg/L and ~750 ng/L standard solutions of MC-LR, respectively

| MC-LR concentration - 750 ng/L | Percent recovery (%) | RSD for signal intensity (%) |
|---|---|---|
| Spiked HPLC-grade water | | |
| Cartridge 1 | 99.01 | 2.65 |
| Cartridge 2 | 99.24 | 2.19 |
| Cartridge 3 | 99.84 | 2.64 |
| Average recovery (%) | 99.37 | |
| RSD for recovery (%) | 2.20 | |
| Spiked river water | | |
| Cartridge 1 | 98.00 | 2.02 |
| Cartridge 2 | 98.35 | 2.25 |
| Cartridge 3 | 98.52 | 2.92 |
| Average recovery (%) | 98.29 | |
| RSD for recovery (%) | 2.10 | |
| MC-LR concentration - 1.25 µg/L | Percent recovery (%) | RSD for signal intensity (%) |
| Spiked HPLC-grade water | | |
| Cartridge 1 | 98.65 | 3.83 |
| Cartridge 2 | 99.85 | 0.79 |
| Cartridge 3 | 98.35 | 3.33 |
| Average recovery (%) | 98.95 | |
| RSD for recovery (%) | 2.63 | |
| Spiked river water | | |
| Cartridge 1 | 98.48 | 2.16 |
| Cartridge 2 | 98.12 | 4.68 |
| Cartridge 3 | 97.55 | 2.90 |
| Average recovery (%) | 97.89 | |
| RSD for recovery (%) | 3.00 | |

The SPE method demonstrates higher recovery of MC-LR as well as better reproducibility and accuracy than known methods for MC-LR preconcentration. In addition, the excellent percent recoveries of MC-LR in both HPLC-grade and river water indicate the developed SPE method can be used for quantification of MC-LR in more complex samples.

Figure 5A:
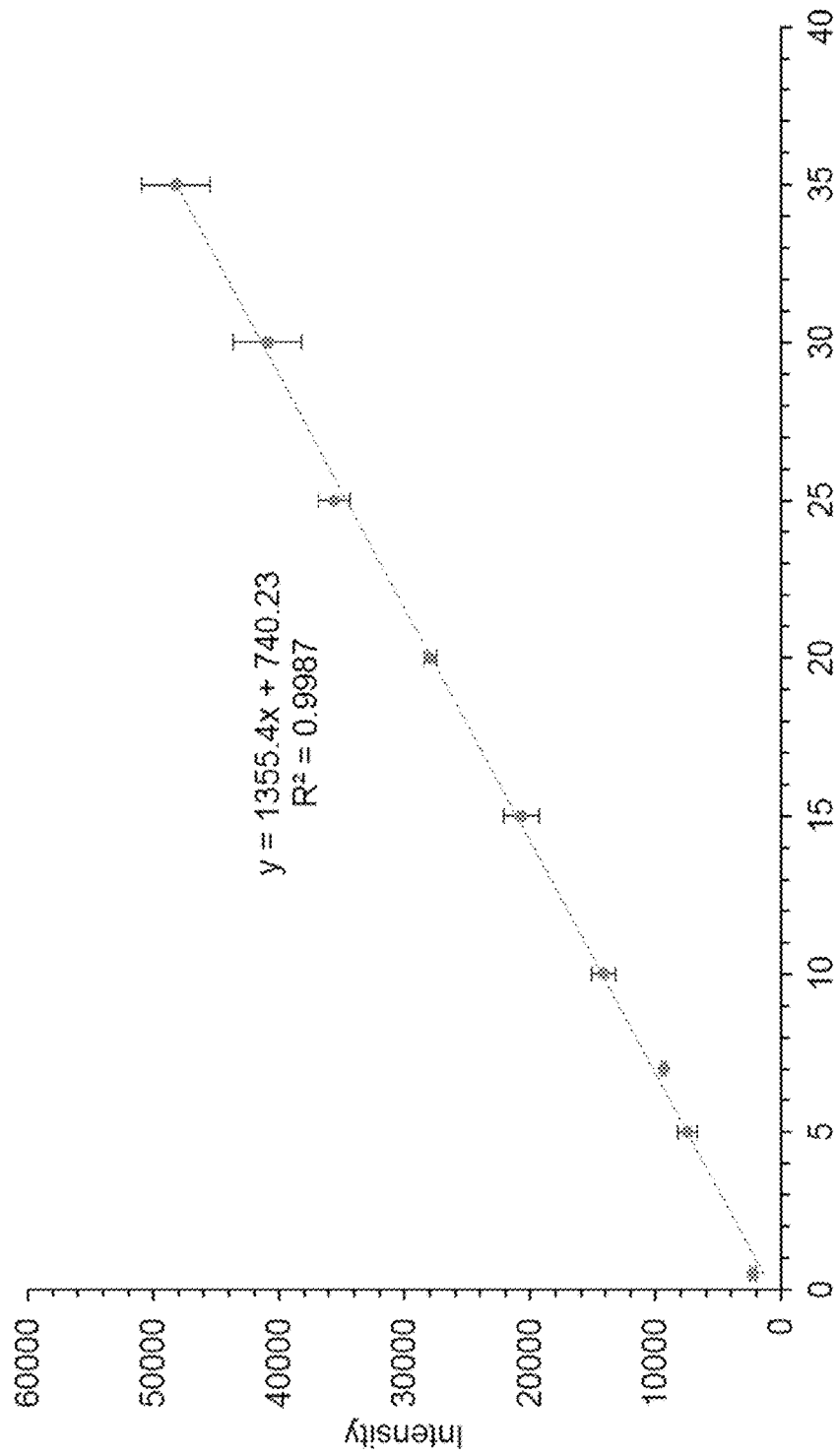
Figure 5B:
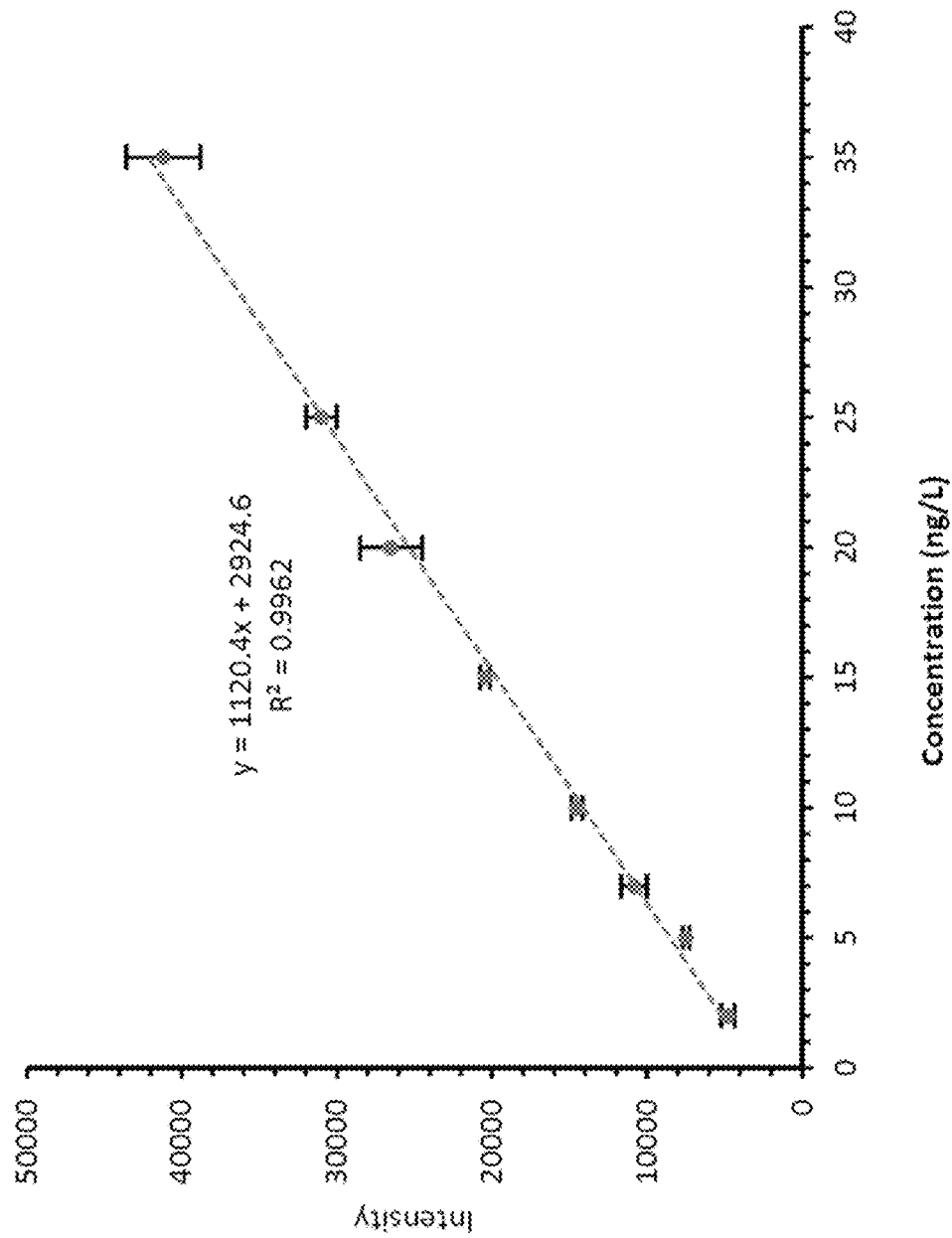
Figure 6A:
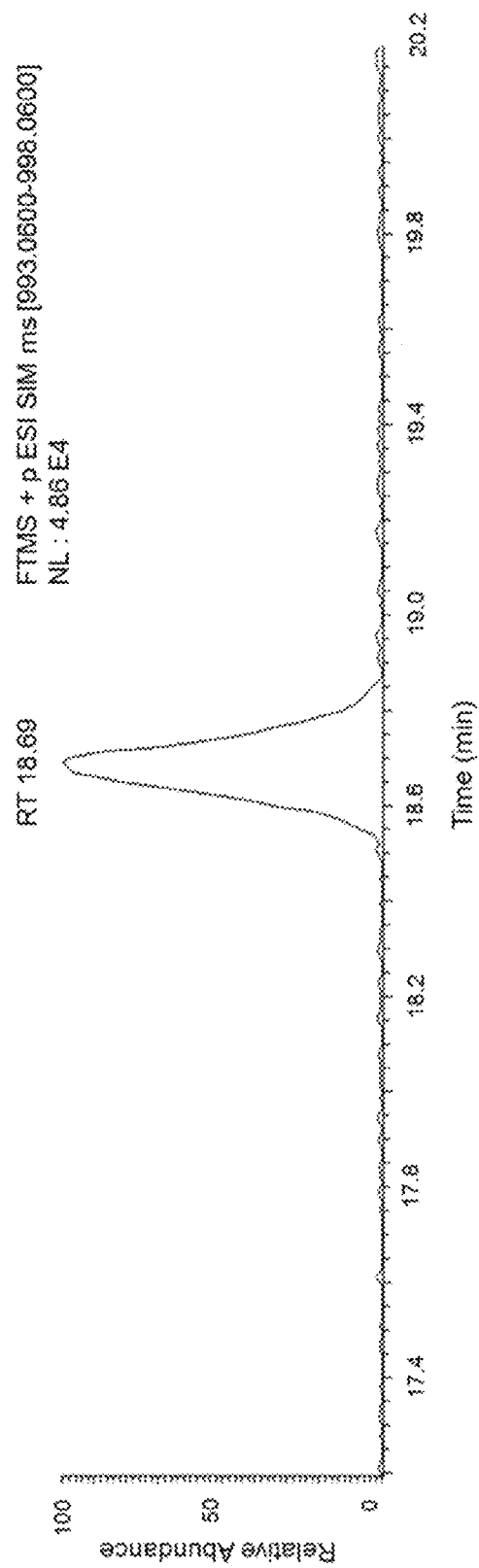
Figure 6B:
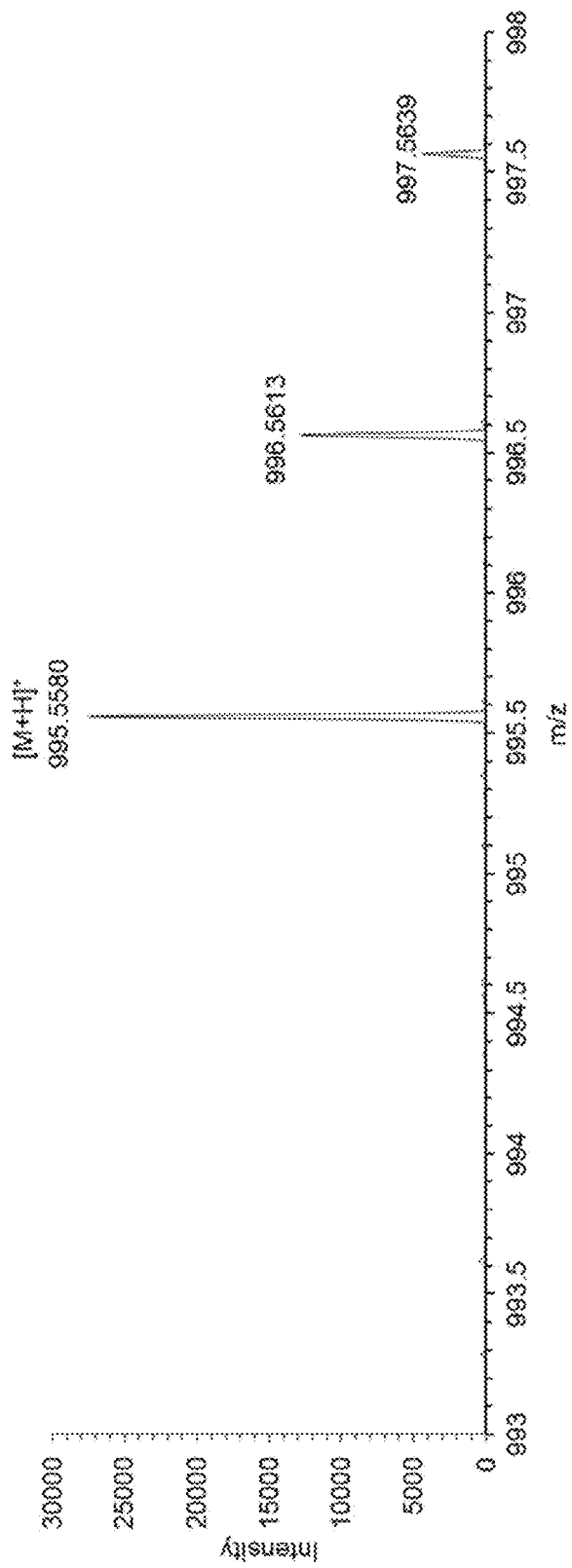

To apply the preconcentration method developed for quantification of low amounts of MC-LR in water, LC-SIM-MS calibration curves were constructed after the purification and preconcentration of the MC-LR samples (FIGS. 5A-5B). FIGS. 6A-6B show the EIC and mass spectrum of a 20 ng/L solution of MC-LR after 50× preconcentration. The concentration of MC-LR solution after preconcentration was ~1 µg/L, and LC-SIM-MS can be readily used to analyze such concentrations of MC-LR as demonstrated previously (FIGS. 2-3).

Figure 7A:
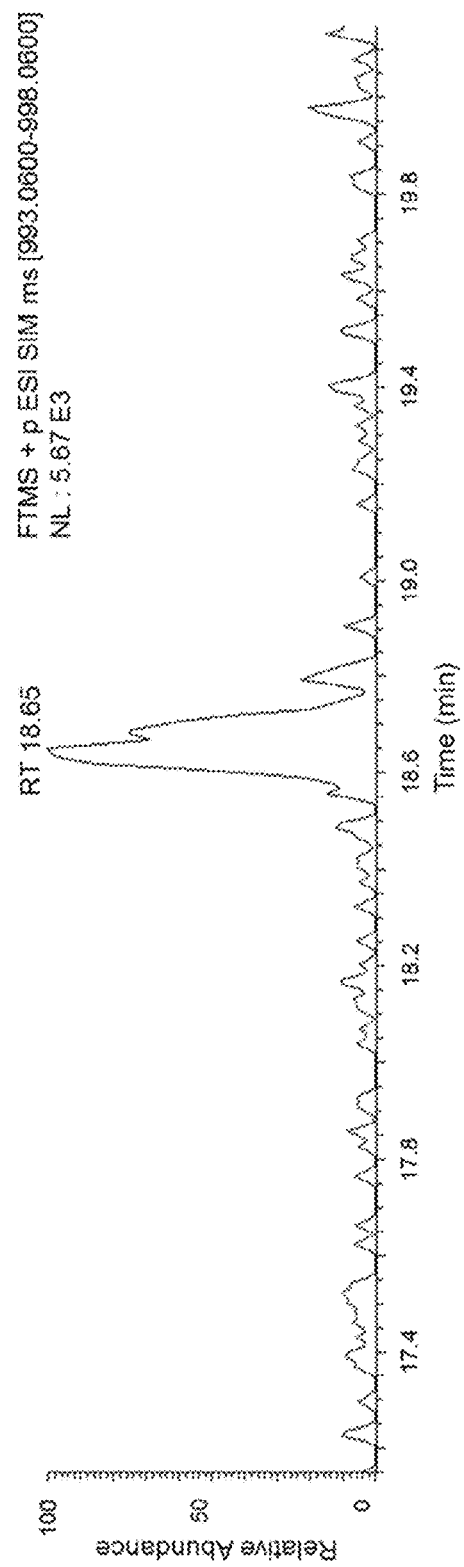
Figure 7B:
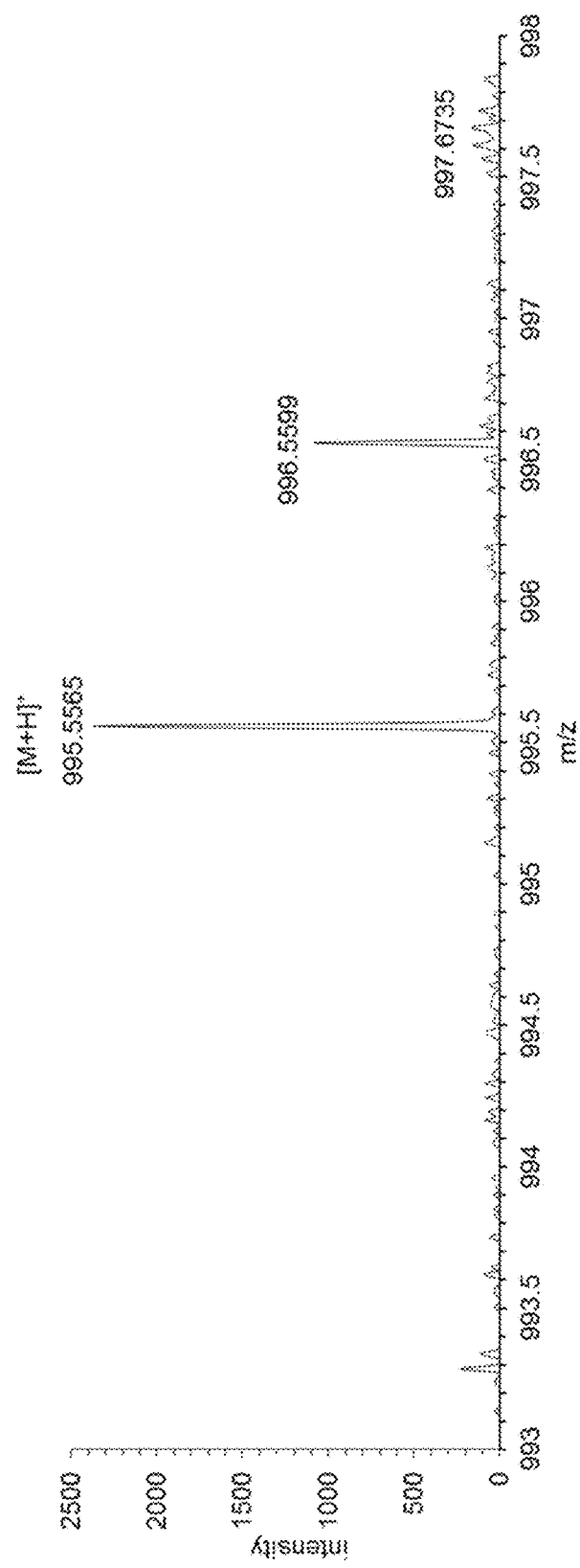

The calibration curve shown in FIG. 5A was obtained for SPE purified MC-LR samples in tap water for quantification of MC-LR in the concentration range between 500 pg/L and 35 ng/L. These concentrations are the initial concentrations of the sample before preconcentration, and the final concentration range after preconcentration was ~25 ng/L-1.75 µg/L. The calibration curve is linear with an $R^2$ value of 0.9987 over this concentration range. SPE purification and preconcentration of the samples prior to LC-SIM-MS analysis permitted detection of MC-LR in very dilute solutions (LOD~300 pg/L). FIGS. 7A-7B show the EIC and mass spectrum for the LOQ of MC-LR (500 pg/L) with preconcentration performed before analysis.

The calibration curve shown in FIG. 5A was validated using a blind standard (Table 2). After triplicate LC-SIM-MS analyses, it was calculated using this calibration curve that the concentration of MC-LR in the unknown samples were 22.77 ng/L (7.92% RSD) and 25.45 ng/L (2.21% RSD) while the actual concentrations were 22.50 ng/L and 25.00 ng/L, respectively. These results indicate that MC-LR can be accurately preconcentrated and quantified in tap water. Therefore, the calibration curve obtained by LC-SIM-MS after preconcentration of MC-LR samples can be used to quantify low (ng/L to pg/L) concentrations of MC-LR in tap water reliably.

Another calibration curve (FIG. 5B) was constructed for quantification of MC-LR in river water in the concentration range between 2 ng/L and 35 ng/L. The concentrations of MC-LR in the four spiked river water samples calculated using this calibration curve were 1.62 ng/L, 4.28 ng/L, 10.35 ng/L, and 20.76 ng/L (Table 3), showing ≤8.11% RSD in comparison to initial concentrations of MC-LR. The LOD of MC-LR in the spiked river water samples was 500 pg/L while MC-LR LOQ was 2.00 ng/L. An increase of MC-LR LOQ in river water in comparison to tap water indicates the suppression of MC-LR ionization at low concentration levels in river water. Without wishing to be bound by theory, it is believed that this may be due to the matrix effects from the other components present in river water samples. Nevertheless, low concentrations of MC-LR were accurately and reproducibly quantified in river water samples.

The validation experiments demonstrate that the developed SPE and LC-ESI-SIM-MS methods can be used for the quantification of MC-LR in complex samples, such as tap and river water.

Validation of Calibration Curves Using Complex MC-LR Samples

Calibration curves shown in FIG. 3 and FIGS. 5A-5B were then applied to quantify MC-LR in more complex samples. Initially, MC-LR was spiked in tap water to prepare a 25.00 ng/L solution of MC-LR, which was then purified by SPE and preconcentrated. Using LC-SIM-MS and the calibration curve in FIG. 5A, it was determined that the concentration of MC-LR in tap water was 25.45 ng/L (2.21% RSD). This result indicates that MC-LR can be accurately preconcentrated and quantified in tap water.

Figure 8:
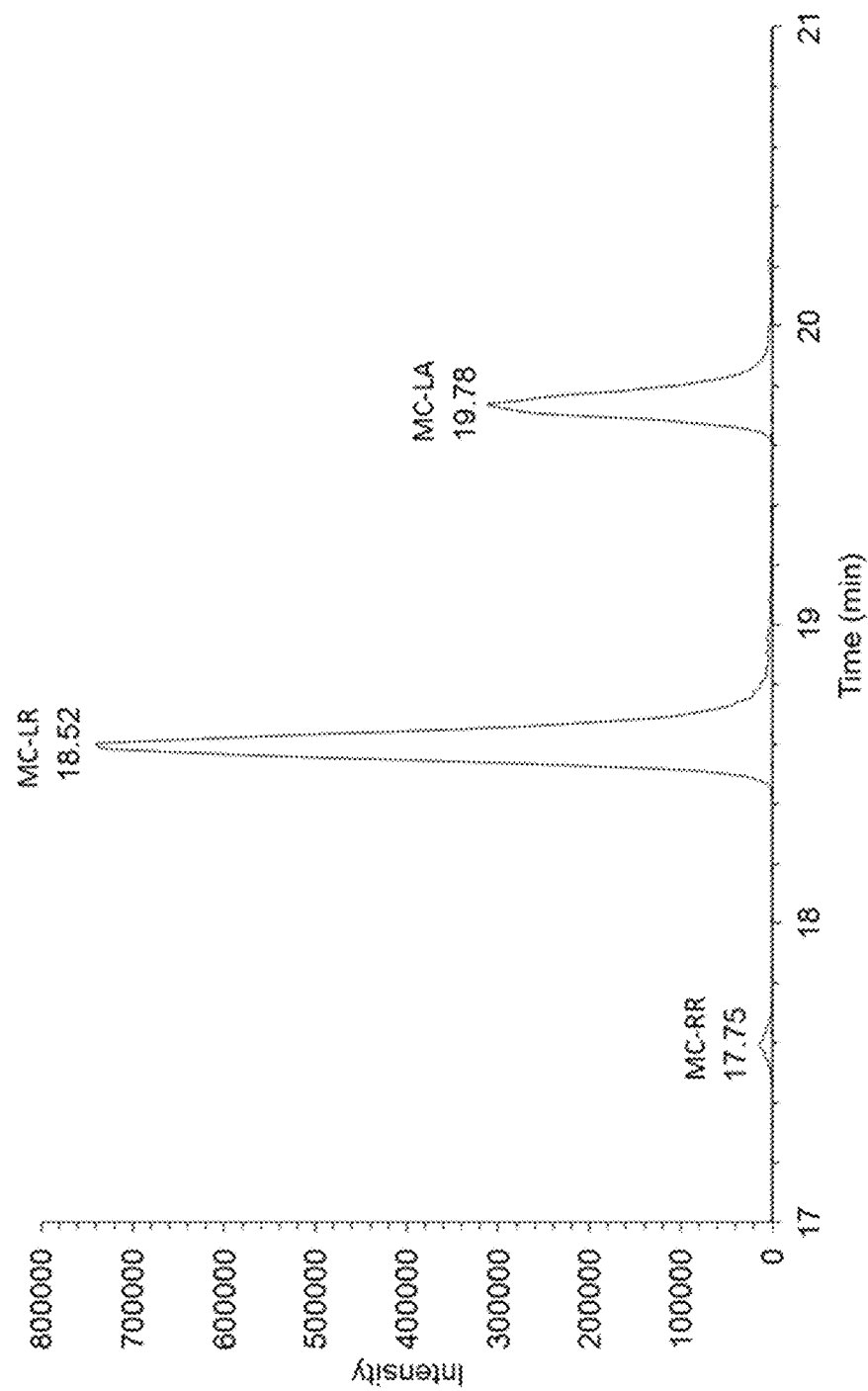
Figure 9A:
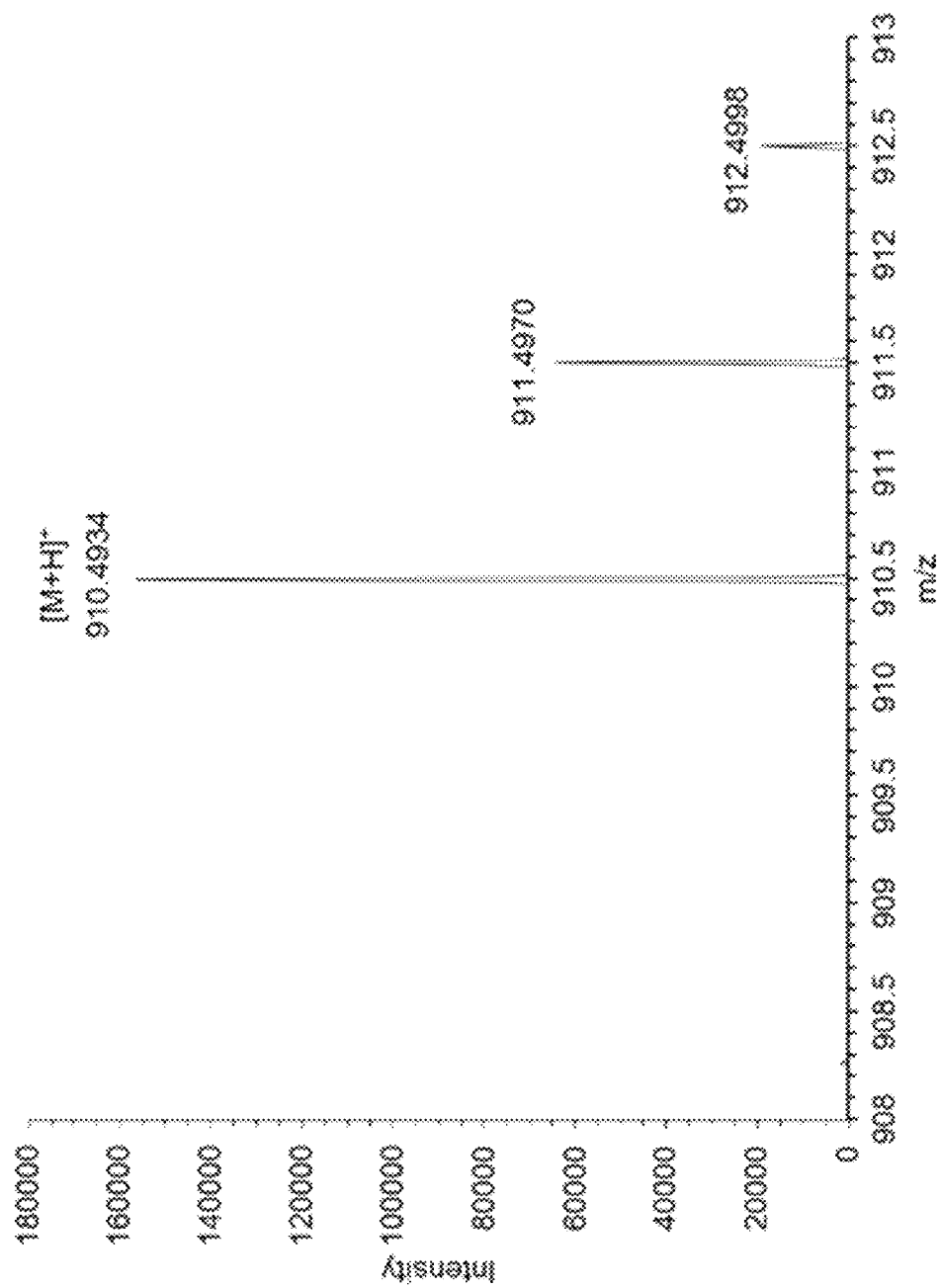
Figure 9B:
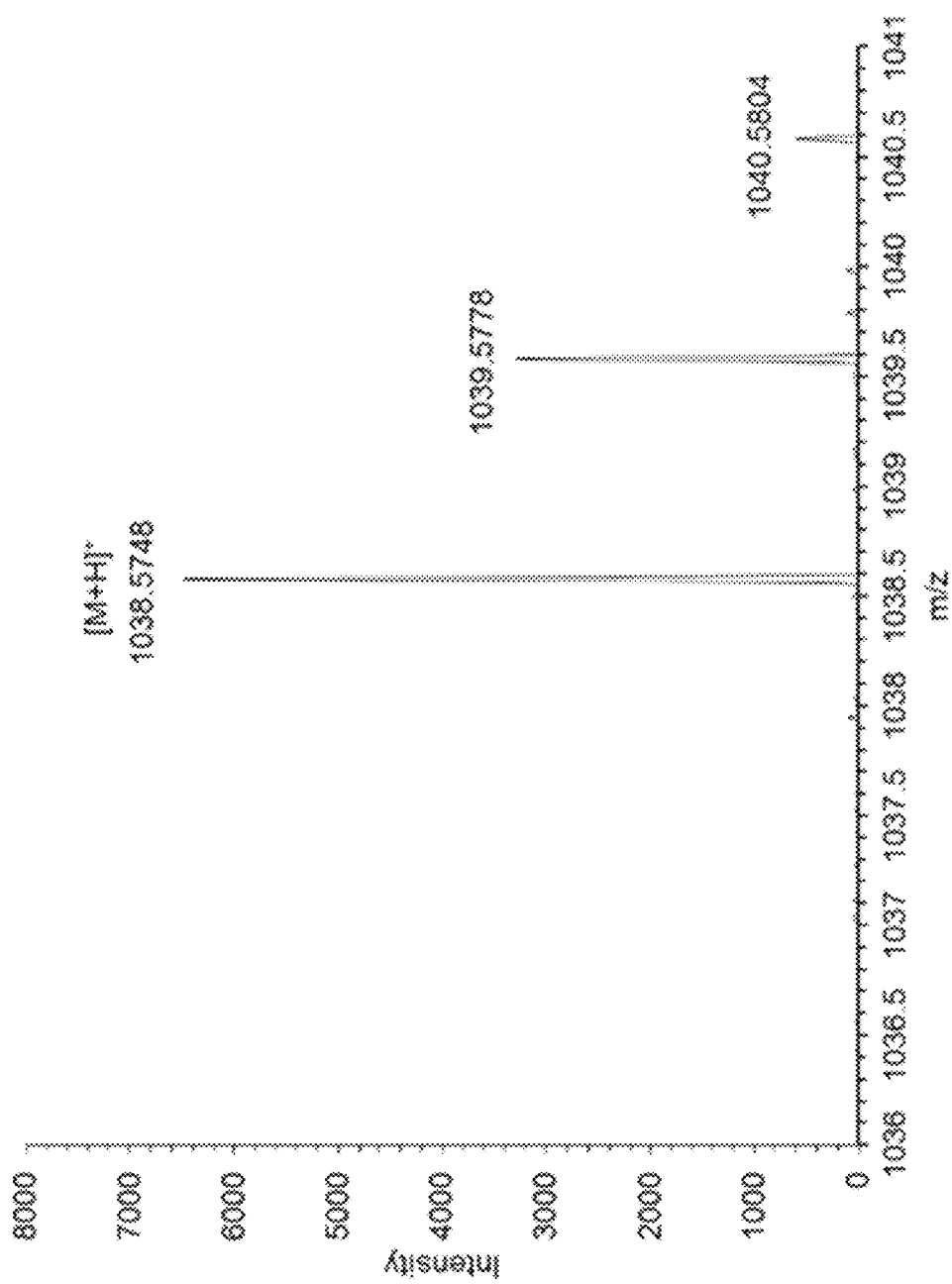

Next, the 10 µg/L solutions of MC-LR, MC-RR, and MC-LA were analyzed individually using LC-SIM-MS of their singly-charged ions whose m/z values are shown in Table 1. FIG. 8 shows the overlaid EICs for MC-RR ($t_R$=17.72 min), MC-LR ($t_R$=18.52 min), and MC-LA ($t_R$=19.78 min). FIGS. 9A-9B shows mass spectra of MC-LA and MC-RR, and m/z values of their singly charged ions were measured with excellent mass accuracies that are <2 ppm (Table 1). Quantification of MC-LR was then performed in a mixture containing 1 µg/L of MC-LR, 1 µg/L of MC-LA, and 10 µg/L MC-RR. The concentration of MC-RR in this solution was higher than the concentration of other MCs due to the low MS peak intensity of its singly charged ion (m/z 1038.5748) at 1 µg/L. Since pure stock solutions of MCs were used for preparation of the mixture, sample purification using SPE was not necessary before the LC-SIM MS analysis. The concentration of MC-LR in the mixture with other MCs was measured using LC-SIM-MS of MC-LR ion with m/z 995.56 and the calibration curve in FIG. 3 was 0.97 µg/L (Table 2), showing 2.18% RSD in comparison to initial concentration of MC-LR (1.00 µg/L). This demonstrated that the developed LC-ESI-SIM-MS method can be used for the quantification of MC-LR in the presence of other MCs without matrix effects occurring.

Quantification of MC-LR Using LC-MS/MS

Figure 10A:
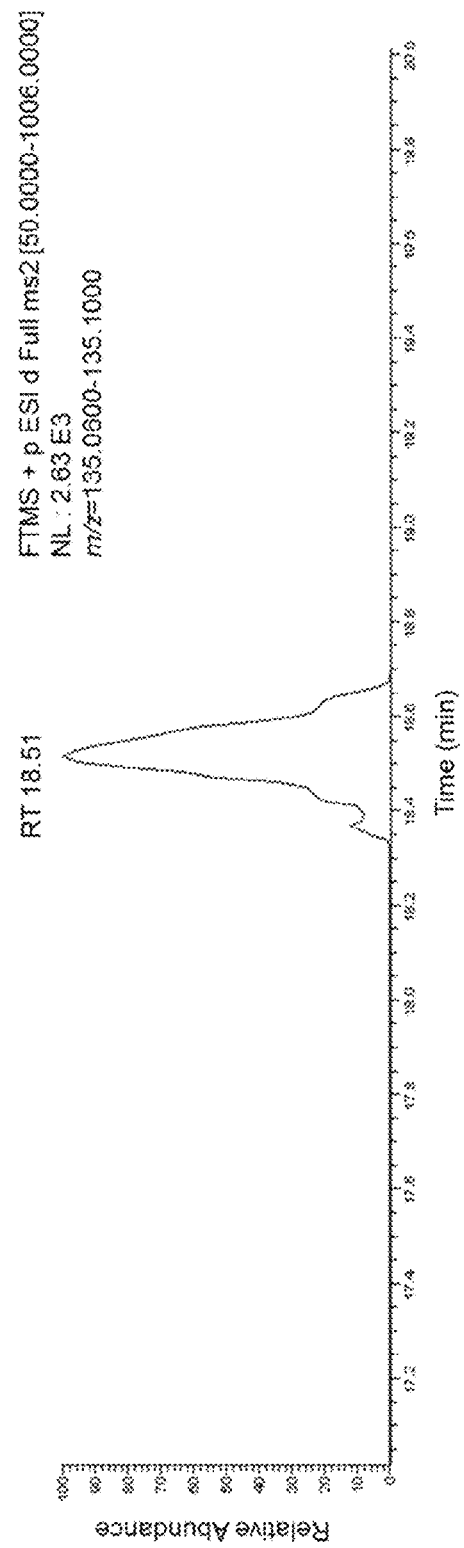
Figure 10B:
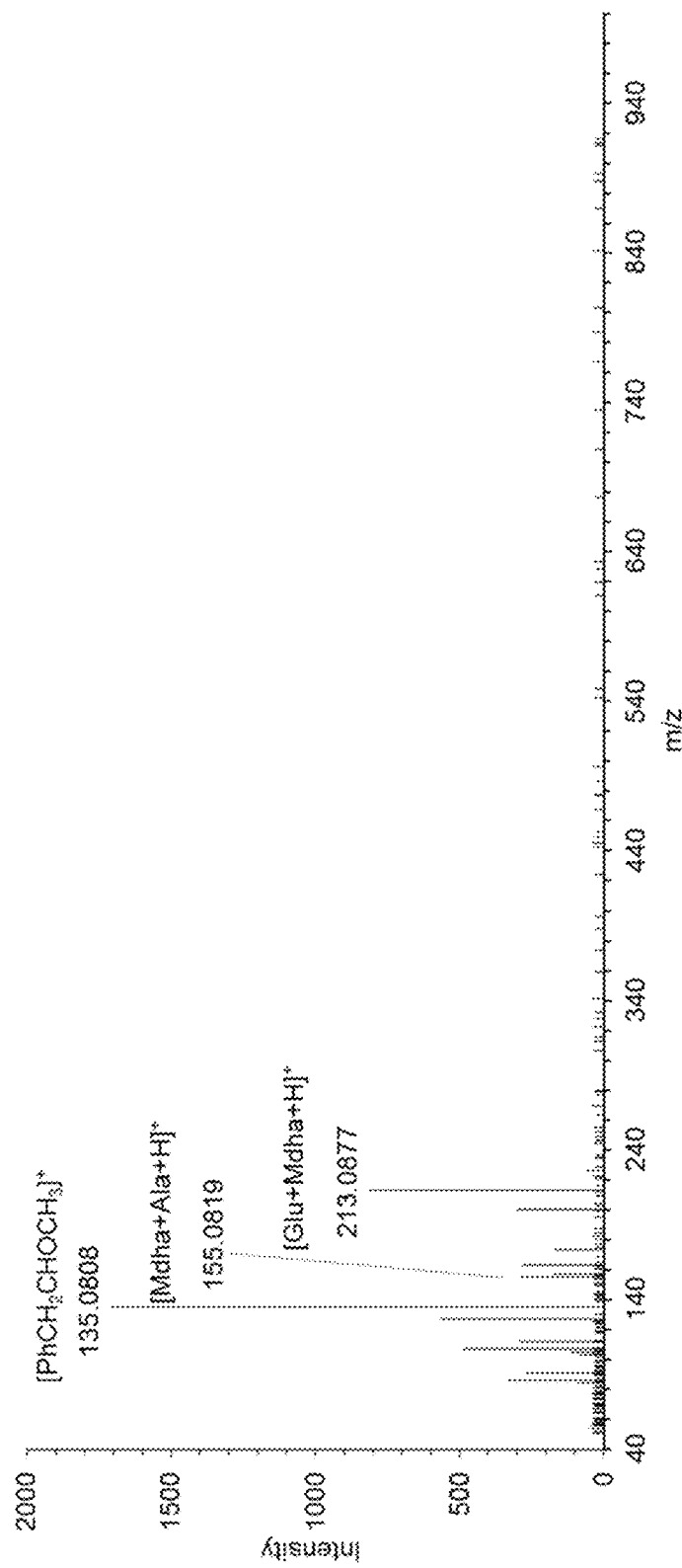

Since the Orbitrap Fusion MS can select ions using SIM and analyze their fragments by MS/MS, the quantification of MC-LR was also performed using LC-MS/MS. Initially, LC-MS/MS was used to analyze aqueous solutions of MC-LR that were not preconcentrated. FIG. 10 shows the EIC of MC-LR fragment ion with m/z 135.0808 and MS/MS spectrum of precursor MC-LR ion (m/z 995.5587) obtained using HCD. The ESI-MS/MS intensities of the MC-LR fragment ion with m/z 135.0808 were determined for standard solutions of MC-LR, and used to construct the LC-MS/MS calibration curve shown in FIG. 11. This calibration curve showed excellent linearity ($R^2$=0.9999) over the concentration range 200 ng/L-10 µg/L. The LOD of MC-LR using LC-MS/MS was ~100 ng/L, and the LOQ of MC-LR was determined to be 200 ng/L. The LOQ of MC-LR using LC-MS/MS is higher than the LOQ measured using LC-SIM-MS (25 ng/L). However, LC-MS/MS is useful for structural characterization and identification of MC variants, and can avoid potential isobaric interferences during the quantification of MC-LR.

FIG. 12 shows the calibration curve constructed using LC-MS/MS for MC-LR solutions with concentrations between 7 ng/L and 35 ng/L, which were preconcentrated 50× yielding final concentration of the standards from ~350 ng/L to ~1.75 µg/L. The calibration curve is linear ($R^2$=0.9974), with a LOQ of 7 ng/L. The LOD of MC-LR using sample preconcentration and LC-MS/MS was ~5 ng/L. The LOQ of MC-LR using LC-MS/MS to analyze preconcentrated MC-LR samples was higher than the LOQ measured using LC-SIM-MS (500 pg/L). LC-SIM-MS was more sensitive for the quantification of low-concentration MC-LR samples than LC-MS/MS. However, the Orbitrap Fusion Tribrid MS can quantify MC-LR at the concentrations that are lower than the maximum concentration of total MCs in drinking water advised by EPA (≤0.3 µg/L) by both LC-SIM-MS and LC-MS/MS. The LOQ of MC-LR by LC-MS/MS may be improved by using LIT instead of orbitrap for quantification. Additional optimizations of HPLC separation conditions and MS acquisition methods may help improving LOQs of MC-LR by both LC-MS and LC-MS/MS further.

A Comparison of Present MC-LR Quantification Results with Literature Data

Due to the differences in the sample complexities as well as the instruments and data processing methods used, it is not straightforward to accurately compare the figures of merit (e.g., LOQs, LODs, and SPE recoveries) of the present methods to those reported previously for the quantification of MC-LR. The present example demonstrates that an HPLC-Orbitrap Fusion MS system provides excellent LOQ and LOD of MC-LR with and without sample preconcentration. Table 6 (FIG. 20) shows a comparison of SPE percent recoveries, LODs and LOQs of MC-LR obtained by different LC-ESI-MS and LC-ESI-MS/MS methods, where the circled methods and the results are from the examples herein. Note that most of the LOD and LOQ values in Table 6 are shown in g/L (ppb), while some are shown in ng/L (ppt).

Additionally, the present SPE purification method exhibits excellent recovery of MC-LR. The MC-LR preconcentration method described in this example is applicable for detection and quantification of MC-LR by LC-MS (or other techniques) in drinking water and more complex, environmental water samples. Importantly, LC-SIM-MS and high-mass accuracy capabilities of an orbitrap mass spectrometer are useful for the targeted quantitative analyses of microcystins. The HPLC-Orbitrap Fusion MS system can also be applied for qualitative and quantitative analyses of multiple microcystins in the full scan mode.

Conclusion

Reproducible and sensitive LC-ESI-SIM-MS and LC-ESI-MS/MS methodologies based on external calibration were developed for the quantification of MC-LR in aqueous solutions, tap water, and a mixture with MC-LA and MC-RR using an HPLC-Orbitrap Fusion MS System. The described sample purification and preconcentration method based on SPE reproducibly and accurately recovered MC-LR from aqueous solutions and tap water for consequent quantitative analyses. MC-LR was detected and quantified using LC-ESI-SIM-MS at high-pg/L and low-ng/L concentrations with and without preconcentration before the analyses, respectively. The LC-ESI-MS/MS method also enabled quantification of MC-LR in the ng/L concentration range. Based on the present results, HPLC-Orbitrap Fusion MS system and preconcentration method developed is useful for efficient LC-MS and LC-MS/MS qualitative and quantitative analyses of MC-LR and other microcystins in water.

Example 2—HPLC Method for the Separation of MCs

A method was developed to separate multiple microcystins in a mixture. FIGS. 13A-13B show the solvent parameters and conditions for the HPLC method utilized in this example, where the solvents were acetonitrile in Pump B and 0.1% formic acid in Pump A.

FIG. 14 shows ion chromatograms for a mixture of MCs. FIGS. 15A-15F show the calibration curves without preconcentration (25 pt to 1 ppb). FIG. 16 shows Table 5, displaying the solid phase extraction recovery data using one SPE cartridge. FIGS. 17A-17F show the calibration curves with preconcentration (500 ppq to 20 ppt). As seen from these results, the method was able to separate six MC species (MC-LR, MC-LA, MC-LF, MC-LW, MC-YR, and MC-RR) with significantly improved LOQs.

Certain embodiments of the methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for detecting and quantifying a microcystin compound in a sample, the method comprising:

preconcentrating a sample containing a microcystin compound at a first concentration through a solid-phase extraction to obtain a preconcentrated sample containing the microcystin compound at a second concentration, wherein the second concentration is higher than the first concentration;

conducting a quantitative analysis on the preconcentrated sample to quantify the amount of microcystin in the preconcentrated sample, wherein the quantitative analysis comprises a liquid chromatography step and a mass spectrometry step using an orbitrap mass analyzer with a quadrupole and a linear ion trap; and using a calibration curve to determine the concentration of the microcystin compound in the sample;

wherein the preconcentrating comprises:

a) conditioning a solid-phase extraction cartridge with a first mixture comprising methanol, water and formic acid;

b) equilibrating the sample in a second mixture comprising water and formic acid;

c) loading the sample of step b) in the conditioned solid phase extraction cartridge of step a); and d) eluting the loaded sample of step c) with a third mixture comprising acetonitrile, water and formic acid.

2. The method of claim 1, wherein the sample contains multiple microcystin compounds, and the liquid chromatography step separates the multiple microcystin compounds.

3. The method of claim 1, wherein the liquid chromatography step comprises gradient high-performance liquid chromatography.

4. The method of claim 1, wherein the microcystin compound is selected from the group consisting of MC-LR, MC-LA, MC-LF, MC-LW, MC-YR, and MC-RR.

5. A method for detecting and quantifying a microcystin compound in a sample, the method comprising:

separating a microcystin species from other microcystin species in a sample containing a plurality of microcystin species through high-performance liquid chromatography (HPLC), creating a gradient mobile phase over time by exposing the sample to a mixture of acetonitrile, water and, formic acid, to separate the microcystin species; and conducting mass spectrometry on the separated microcystin species to quantify the amount of the separated microcystin species, wherein the mass spectrometry uses an orbitrap mass analyzer with a quadrupole and a linear ion trap; and using a calibration curve to determine the concentration of the separated microcystin species in the sample;

the method further comprising a preconcentrating step prior to the separating, wherein the preconcentrating step comprises preconcentrating the sample containing the plurality of microcystin species at a first concentration through a solid-phase extraction to obtain a preconcentrated sample containing the plurality of microcystin species at a second concentration, wherein the second concentration is higher than the first concentration;

wherein the preconcentrating step comprises:

a) conditioning a solid phase extraction cartridge with methanol containing formic acid;

b) equilibrating the sample in water containing formic acid;

c) loading the sample in the conditioned solid phase extraction cartridge;

and d) eluting the loaded sample with acetonitrile containing formic acid.

6. The method of claim 5, wherein the plurality of microcystin species includes two or more of MC-LR, MC-LA, MC-LF, MC-LW, MC-YR, and MC-RR.

7. A method of preconcentrating microcystins in a sample, the method comprising:

conditioning a solid phase extraction (SPE) cartridge with a first mixture comprising methanol, water, and formic acid;

loading a sample containing microcystins at a first concentration onto the solid phase extraction cartridge;

eluting the sample with a second mixture comprising acetonitrile, water and formic acid, and collecting the eluted sample;

evaporating the solvent from the eluted sample to obtain an evaporated sample, and redissolving the sample in the solvent to obtain a preconcentrated sample, wherein the preconcentrated sample contains microcystin at a second concentration, the second concentration being greater than the first concentration.

8. The method of claim 7, further comprising washing the SPE cartridge with water containing formic acid.

9. The method of claim 7, further comprising a washing step.

10. The method of claim 7, wherein the SPE cartridge is a C18 cartridge.

11. The method of claim 7, wherein the sample comprises a plurality of microcystin species.

12. The method of claim 11, wherein the plurality of microcystin species includes two or more of MC-LR, MC-LA, MC-LF, MC-LW, MC-YR, and MC-RR.

* * * * *